(12) United States Patent
Knueppel

(10) Patent No.: US 9,084,645 B2
(45) Date of Patent: *Jul. 21, 2015

(54) BONE FIXATION ASSEMBLY

(75) Inventor: Stefan Knueppel, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 564 days.

This patent is subject to a terminal disclaimer.

(21) Appl. No.: 13/364,634

(22) Filed: Feb. 2, 2012

(65) Prior Publication Data

US 2012/0197257 A1    Aug. 2, 2012

Related U.S. Application Data

(63) Continuation-in-part of application No. 13/019,907, filed on Feb. 2, 2011.

(51) Int. Cl.
| | | |
|---|---|---|
| *A61B 17/82* | (2006.01) | |
| *A61B 17/88* | (2006.01) | |
| *B65B 13/02* | (2006.01) | |
| *A61B 17/04* | (2006.01) | |
| *A61B 17/06* | (2006.01) | |

(Continued)

(52) U.S. Cl.
CPC ........... *A61B 17/823* (2013.01); *A61B 17/8863* (2013.01); *A61B 17/8869* (2013.01); *B65B 13/027* (2013.01); *A61B 2017/00407* (2013.01); *A61B 2017/0454* (2013.01); *A61B 2017/0496* (2013.01); *A61B 2017/06052* (2013.01); *A61B 2019/302* (2013.01)

(58) Field of Classification Search
CPC . A61B 17/82; A61B 17/8861; A61B 17/8869

USPC .............. 606/74, 300, 324, 103, 113, 117, 606/86 A–86 R, 99, 905, 139–141, 157–158, 606/37; 433/4, 39–40, 155; 140/123.5–123.6, 93 R, 93.2; 269/3, 6, 269/95; 254/245–246

See application file for complete search history.

(56) References Cited

U.S. PATENT DOCUMENTS

| | | |
|---|---|---|
| 3,570,497 A | 3/1971 | Lemole |
| 3,577,601 A | 5/1971 | Mariani et al. |

(Continued)

FOREIGN PATENT DOCUMENTS

| | | |
|---|---|---|
| DE | 3244680 | 6/1984 |
| DE | 3538645 | 5/1987 |

(Continued)

*Primary Examiner* — Anu Ramana
*Assistant Examiner* — Jessica Weiss
(74) *Attorney, Agent, or Firm* — Baker & Hostetler LLP

(57) ABSTRACT

A bone fixation system includes at least one bone fixation member and a bone fixation instrument. The bone fixation member includes a strap and a locking mechanism. The strap can be pulled through the locking mechanism so as to form a loop about a target bone so as to secure first and second bone segments in an approximated, compressed configuration. The bone fixation instrument is configured to apply tension to the loop about the target bone. The fixation instrument includes a tension assembly that is configured to secure a free end of the bone fixation member to the fixation instrument. The tension assembly is further configured to pull the free end so as to increase tension in the loop while the tension in the loop is less than a select tension. The fixation instrument further includes a cutter assembly.

20 Claims, 21 Drawing Sheets

(51) Int. Cl.
*A61B 17/00* (2006.01)
*A61B 19/00* (2006.01)

(56) References Cited

U.S. PATENT DOCUMENTS

| | | | |
|---|---|---|---|
| 3,645,302 A * | 2/1972 | Caveney et al. | 140/93.2 |
| 3,661,187 A | 5/1972 | Caveney et al. | |
| 3,830,263 A * | 8/1974 | Benfer | 140/93.2 |
| 4,093,005 A | 6/1978 | Eberhardt et al. | |
| 4,535,764 A | 8/1985 | Ebert | |
| 4,730,615 A | 3/1988 | Sutherland et al. | |
| 4,813,416 A | 3/1989 | Pollak et al. | |
| 4,955,913 A | 9/1990 | Robinson | |
| 5,146,645 A | 9/1992 | Dirksing | |
| 5,146,654 A | 9/1992 | Caveney et al. | |
| 5,193,250 A | 3/1993 | Caveney | |
| 5,355,913 A | 10/1994 | Green et al. | |
| 5,356,417 A | 10/1994 | Golds | |
| 5,361,475 A * | 11/1994 | Scruggs | 29/267 |
| 5,366,461 A | 11/1994 | Blasnik | |
| 5,383,882 A | 1/1995 | Suess et al. | |
| 5,392,822 A | 2/1995 | Kraus | |
| 5,403,346 A | 4/1995 | Loeser | |
| 5,437,685 A | 8/1995 | Blasnik | |
| 5,462,542 A | 10/1995 | Alesi, Jr. | |
| 5,496,318 A | 3/1996 | Howland et al. | |
| 5,549,619 A | 8/1996 | Peters et al. | |
| 5,571,105 A | 11/1996 | Gundolf | |
| 5,607,430 A | 3/1997 | Bailey | |
| 5,636,412 A | 6/1997 | Lodi et al. | |
| 5,665,088 A | 9/1997 | Gill et al. | |
| 5,665,089 A | 9/1997 | Dall et al. | |
| 5,683,404 A | 11/1997 | Johnson | |
| 5,741,259 A | 4/1998 | Chan | |
| 5,772,663 A | 6/1998 | Whiteside et al. | |
| 5,810,824 A | 9/1998 | Chan | |
| 5,915,425 A | 6/1999 | Nilsson et al. | |
| 5,972,006 A | 10/1999 | Sciaino, Jr. | |
| 6,049,949 A | 4/2000 | Guthke | |
| 6,050,998 A | 4/2000 | Fletcher | |
| 6,099,527 A | 8/2000 | Hochschuler et al. | |
| 6,302,889 B1 | 10/2001 | Keller | |
| 6,489,246 B1 | 12/2002 | Summa et al. | |
| 6,514,255 B1 | 2/2003 | Ferree | |
| 6,520,965 B2 | 2/2003 | Chervitz et al. | |
| 6,589,246 B1 | 7/2003 | Hack et al. | |
| 7,008,429 B2 | 3/2006 | Golobek | |
| 7,112,221 B2 | 9/2006 | Harris | |
| 7,164,360 B2 | 1/2007 | Schiebler | |
| 7,229,444 B2 | 6/2007 | Boyd | |
| 7,481,828 B2 | 1/2009 | Mazda et al. | |
| 7,582,089 B2 | 9/2009 | Schiebler | |
| 7,648,504 B2 | 1/2010 | Heino et al. | |
| 2003/0236538 A1 | 12/2003 | Aikens | |
| 2004/0059357 A1 | 3/2004 | Koseki | |
| 2004/0068292 A1 | 4/2004 | Koseki | |
| 2006/0142772 A1 | 6/2006 | Ralph et al. | |
| 2007/0055258 A1 | 3/2007 | Hansen | |
| 2007/0093825 A1 | 4/2007 | Ferree | |
| 2007/0260251 A1 | 11/2007 | Weier | |
| 2008/0300599 A1 | 12/2008 | Anapliotis et al. | |
| 2009/0012569 A1 | 1/2009 | Dall et al. | |
| 2009/0270923 A1 | 10/2009 | Tormala et al. | |
| 2009/0326585 A1 | 12/2009 | Baccelli et al. | |

FOREIGN PATENT DOCUMENTS

| | | |
|---|---|---|
| DE | 4021246 | 1/1992 |
| DE | 4024334 | 2/1992 |
| DE | 4200757 | 7/1992 |
| DE | 4127550 | 2/1993 |
| DE | 4314185 | 11/1993 |
| DE | 19716504 | 12/1998 |
| DE | 19806628 | 8/1999 |
| EP | 0009327 | 4/1980 |
| EP | 0201905 | 11/1986 |
| EP | 0299387 | 1/1989 |
| EP | 0512297 | 11/1992 |
| EP | 0587635 | 3/1994 |
| EP | 0597257 | 5/1994 |
| EP | 0608592 | 8/1994 |
| EP | 0780096 | 6/1997 |
| EP | 0858419 | 8/1998 |
| EP | 0876798 | 11/1998 |
| EP | 0937930 | 8/1999 |
| EP | 1564144 | 8/2005 |
| FR | 2677536 | 12/1992 |
| FR | 2690727 | 11/1993 |
| FR | 2702951 | 9/1994 |
| FR | 2906704 | 4/2008 |
| GB | 2266557 | 11/1993 |
| GB | 2414936 | 12/2005 |
| JP | 2004298501 | 10/2004 |
| WO | WO 88/06022 | 8/1988 |
| WO | WO 2006/062419 | 6/2006 |
| WO | WO 2006/136938 | 12/2006 |
| WO | WO 2009/013397 | 1/2009 |
| WO | WO 2009/091313 | 7/2009 |
| WO | WO 2010/041101 | 4/2010 |
| WO | WO 2010/108050 | 9/2010 |
| WO | WO 2012/106505 | 8/2012 |

* cited by examiner

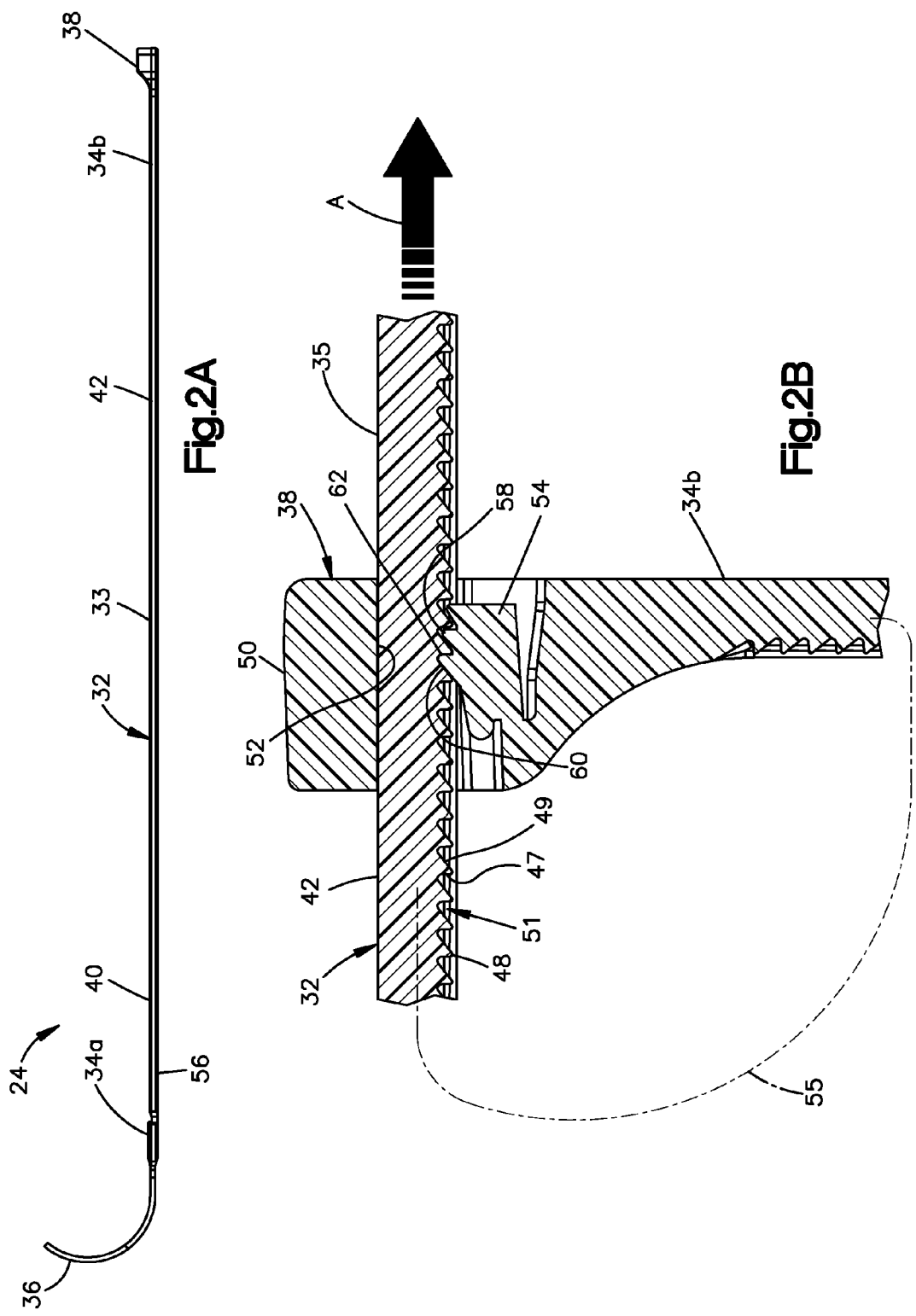

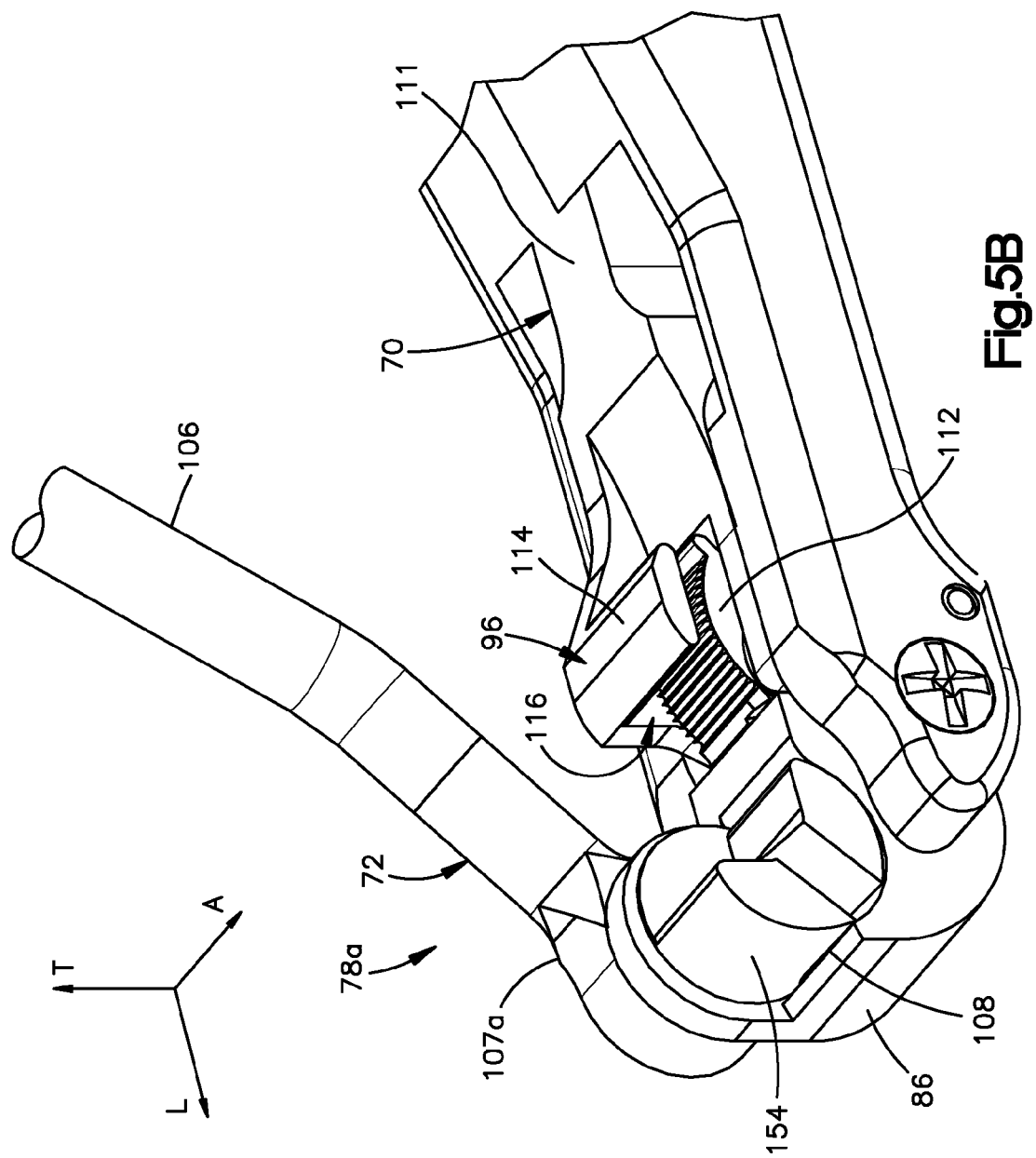

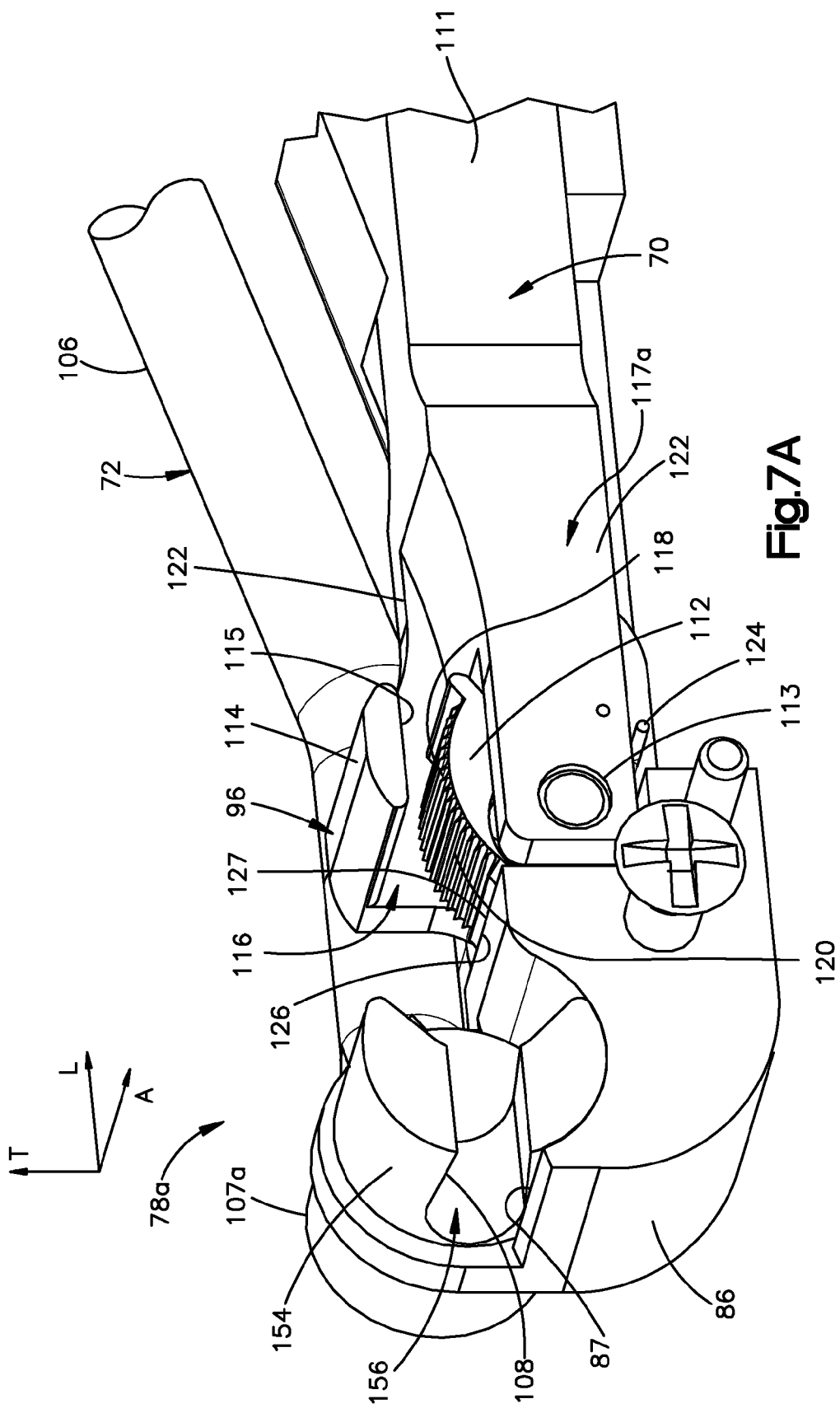

US 9,084,645 B2

BONE FIXATION ASSEMBLY

CROSS-REFERENCE TO RELATED APPLICATIONS

This application is a continuation-in-part of U.S. Ser. No. 13/019,907, filed Feb. 2, 2011, the entire contents of which are incorporated herein by reference.

BACKGROUND

In order to provide access to certain internal anatomy, such as the heart during an open heart procedures, midline sternotomies are typically performed. A midline sternotomy creates a cut substantially along the midline of the sternum, thereby dividing the ribcage into two halves and allowing the surgeon to move the ribcage so as to provide access to the heart. Upon completion of the open heart procedure, it is desired to approximate and compress the sternum, and rigidly maintain the sternal halves in their approximated position relative to each other so that the sterna halves are prevented from moving with respect to each other to promote bone fusion in the weeks following the surgical procedure.

During normal anatomical function, for instance during respiration, body movement, and carrying of objects, forces can be generated that act on the sternum. One conventional system sternal fixation assembly includes stainless steel wires that are placed either parasternally (around the sternum) or transsternally (through the sternum bone) using a cutting needle that is attached to the wire, and subsequently twisted to tighten the wire against the sternum. However, the twisting generates tensile forces onto the wires that tend to weaken the wire, which can result in breakage both during the closure or post-operatively. Furthermore, this type of system relies on the experience of the surgeon when tightening the wires. If the wires are not tightened enough, the sternal compression can be compromised. If the wires are tightened too much, the wire can cut into or through the sternum and/or can break.

SUMMARY

In accordance with one embodiment, a bone fixation instrument is configured to apply tension to a bone fixation member so as to tighten the bone fixation member about a target bone. The bone fixation instrument includes a body that defines a front end and an opposed rear end, a grip configured to secure a free end of the fixation member to the fixation instrument, a traveler that is connected to the grip such that the grip moves rearward along with the traveler so as to increase tension in the bone fixation member, and an actuator operatively coupled to the traveler. The actuator can be configured to move from an initial position toward a tension position in response to an applied force, thereby biasing the traveler to move rearward. The bone fixation instrument can further include a tension limiter connected between the actuator and the traveler. The tension limiter allows the traveler to move rearward when the tension in the bone fixation member is less than the selected tension, and prevents the traveler from moving rearward when the tension in the bone fixation member reaches the selected tension.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 2A is a perspective view of a bone fixation member including a body and a locking member, showing the bone fixation member in an initial configuration;

FIG. 2B is an enlarged perspective view of a portion of the bone fixation member illustrated in FIG. 2A, showing the body inserted through the locking member so as to secure the bone fixation member about an underlying bone;

FIG. 5B is a perspective view of a front end of the bone fixation instrument as illustrated in FIG. 5A;

FIG. 7A is a perspective view of the front end of the bone fixation instrument illustrated in FIG. 4, showing the tension assembly in a disengaged position;

DETAILED DESCRIPTION

Figure 1:
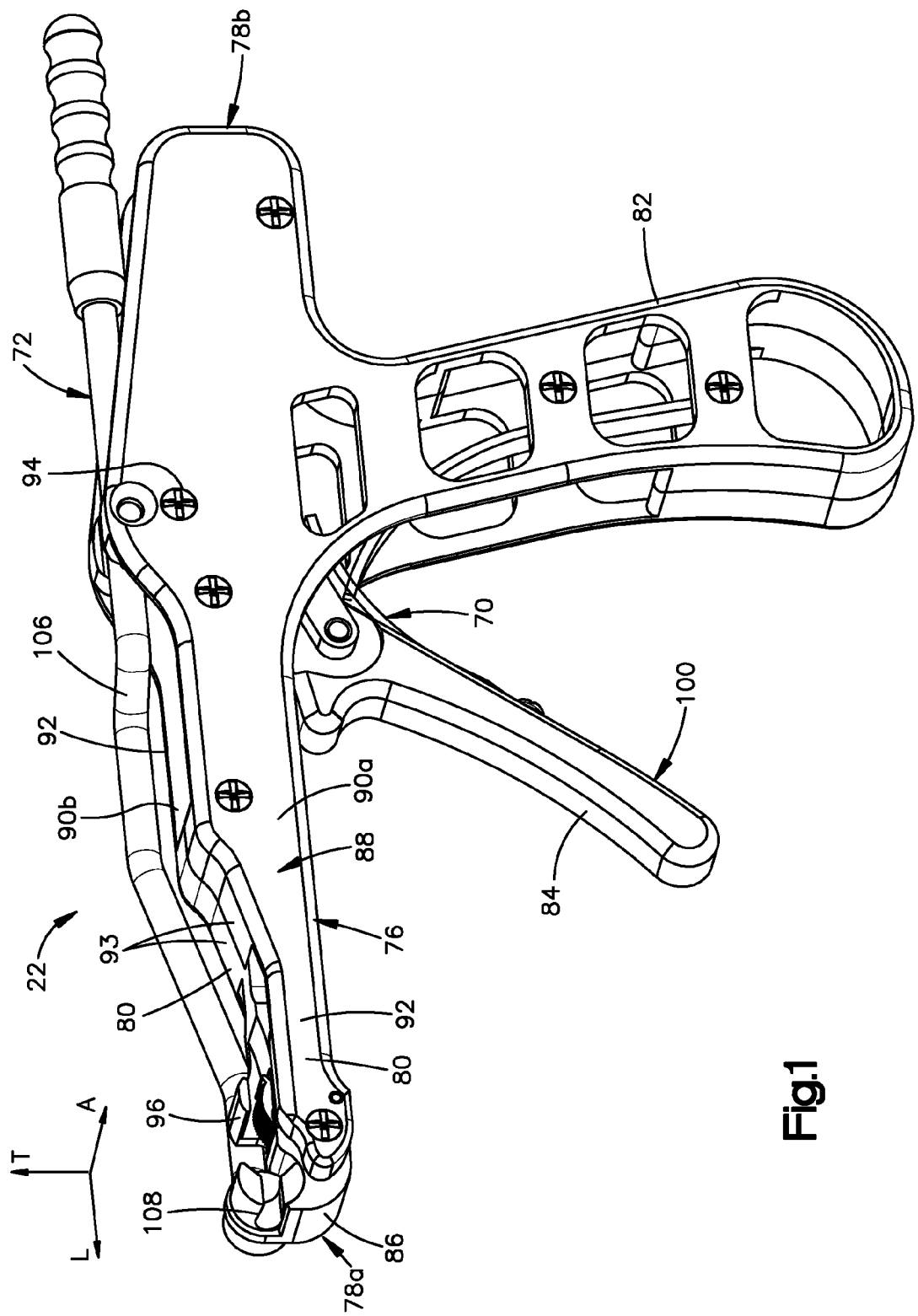
FIG. 1 is a perspective view of a bone fixation instrument constructed in accordance with one embodiment.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1-3B, a bone fixation assembly 20 includes a bone fixation instrument 22 and at least one bone fixation member 24 such as a plurality of bone fixation members 24 that are configured to secure a first and second bone segments 26a and 26b of a target bone 28, such as a sternum, that are separated at a fracture location 30 together in a compressed approximated position.

In accordance with the illustrated embodiment, each bone fixation member 24 can be substantially configured as a cable tie, and can include a flexible strap 32 defines a strap body 33 and has first end 34a and a second end 34b opposite the first end 34a along the length of the strap 32, a needle tip 36 that extends from the first end 34a, and a locking mechanism 38 that extends from the second end 34b. The strap 32 can be made from any suitable biocompatible material as desired, such as PEEK.

Each bone fixation member 24 can further include a first initiation region 40 that extends from the first end 34a toward the second end 34b along a portion of a length of the strap 32 (for instance, approximately ⅓ the length of the strap 32) and a second locking region 42 that extends between the first initiation region 40 and the second end 34b. In accordance with the illustrated embodiment, the second locking region 42 extends from the first initiation region 40 to the second end 34b. The first initiation region 40 can include a plurality of small protrusions that extend out from the strap body 33 and alternate with recessed regions disposed between adjacent protrusions. Alternatively, the initiation region 40 can be substantially smooth and devoid of protrusions or teeth. The second locking region 42 can include a plurality of locking teeth 48 that extend out from the strap body 33 a distance greater than the protrusions and are separated by recessed regions 51 disposed between adjacent locking teeth. It should be appreciated that the locking region 42 can extend along any portion up to all of the strap body 33 as desired.

The locking mechanism 38 includes a housing 50 a strap receiving slot 52 that extends through the housing 50 and is configured to receive the first end 34a of the strap 32. In accordance with the illustrated embodiment, the first end 34a is inserted through the slot 52 so as to define a loop 55 about the target bone 28. The locking mechanism 38 is configured to allow the strap 32 to translate unidirectionally through the slot 52 along the direction of Arrow A so as to reduce the size of the loop 55 about the first and second segments 26a and 26b of the target bone 28. For instance, the needle tip 36 can be inserted through the slot 52 and subsequently removed, for instance by cutting a neck 56 of the strap body 33 that defines reduced thickness at a location adjacent the needle tip 36, such that the strap 32 remains in the slot 52. In accordance with the illustrated embodiment, the locking mechanism 38 includes a locking member such as a tongue 54 that is connected to the housing 50 and includes at least one complementary tooth such as a plurality of locking teeth 58 that extend into the slot 52. The locking teeth 58 define a beveled leading edge 60 that that is configured to cam over complementary beveled leading edges 49 of the locking teeth 48 when the strap 32 is translated through the slot 52 along the direction of Arrow A. The locking teeth 58 and 48 further define trailing edges 62 and 47 that are sloped less than the beveled leading edges 60, such that the trailing edges 62 and 47 engage to prevent the strap 32 from translating through the slot 52 along the direction opposite Arrow A, which would increase the size of the loop 55.

During operation, the strap 32 is wrapped around the first and second segments 26a and 26b of the target bone 28, and the needle tip 36 is inserted through the slot 52 and pulled through the slot 52 so as to cause the strap 32 to subsequently translate through the slot 52. The needle tip 36 can be removed from the strap 32, and the strap 32 can then be further pulled, for instance manually, through the slot 52. As the strap 32 is translated through the locking mechanism 38 along the direction of Arrow A, the small protrusions of the initiation region 40 can slide through the slot 52 without engaging the locking teeth 58 of the locking mechanism 38. As the locking region 42 of the strap 32 is translated through the slot 52 along the direction of Arrow A, the locking teeth 48 and 58 can engage to prevent the tension that is induced in the strap 32 from causing the strap 32 to back out of the slot 52 along a direction opposite Arrow A. For instance, as the strap 32 translates through the locking mechanism 38 along the direction of Arrow A, the size of the loop 55 about the target bone 28 decreases until tactile feedback indicates that tension has been induced in the strap 32.

Figure 3A:
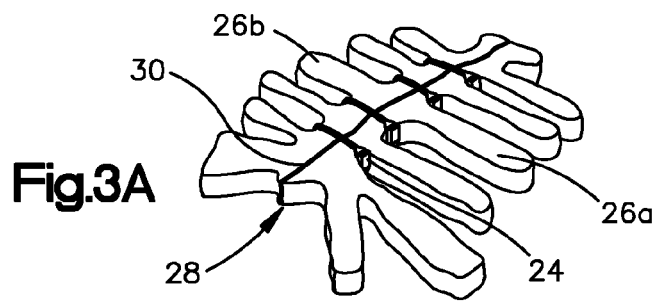
FIG. 3A is a perspective view of a plurality of the bone fixation members illustrated in FIG. 2A shown tightened about a target bone and cut.
Figure 3B:
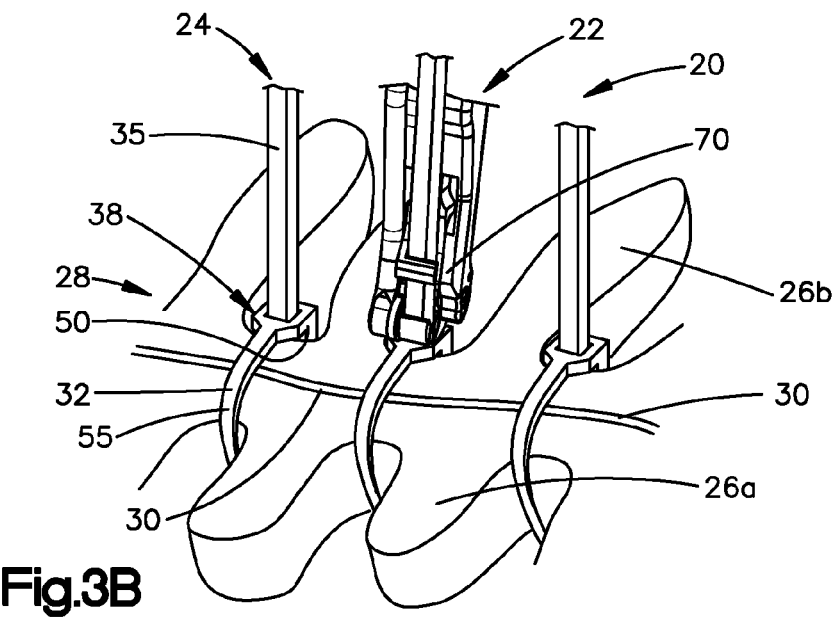
FIG. 3B is a perspective view of the bone fixation instrument illustrated in FIG. 1 operatively coupled to and tightening one of a plurality of the bone fixation members illustrated in FIG. 3A.
Figure 3C:
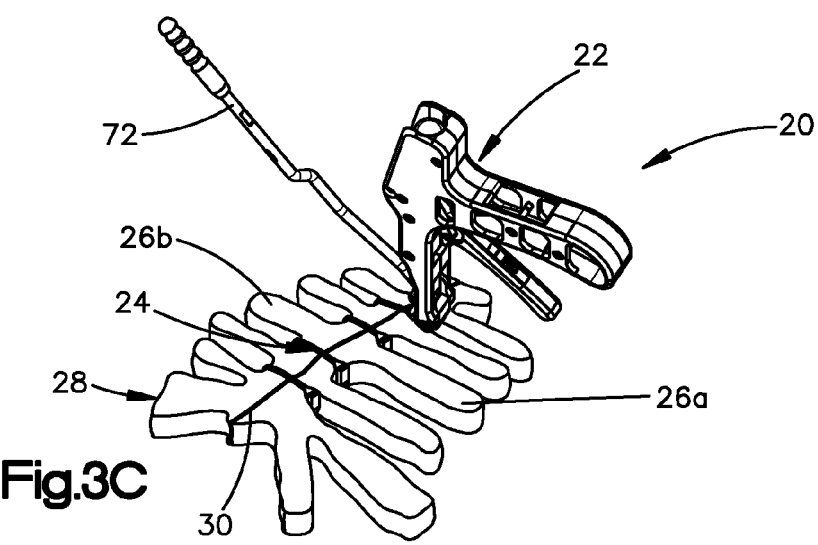
FIG. 3C is a perspective view of the bone fixation instrument illustrated in FIG. 1 operatively coupled to and cutting one of the tightened bone fixation members illustrated in FIG. 3B.

As illustrated in FIG. 3B, the fixation instrument 22 includes a tension assembly 70 that is configured to secure the fixation instrument 22 to the strap 32, and is further configured to further pull the strap 32 through the locking mechanism 38 thereby further inducing tension in the strap 32 until the strap 32 has securely compressed the bone first and second bone segments 26a and 26b of the target bone 28 together at the fracture location 30. As illustrated in FIG. 3C, the fixation instrument 22 further includes a cutter assembly 72 that is configured to cut a free end 35 of the strap 32 that has passed through the locking mechanism 38 once a desired tension has been induced in the strap 32 about the first and second segments 26a and 26b of the target bone 28. For instance, the desired tension can be within a range defined by and between a lower end that can be approximately 50 Newtons or approximately 80 Newtons, and an upper end that can be approximately 150-160 Newtons or 200 Newtons. It should be appreciated that the desired tension can depend on the bone quality and the preference of the surgeon, and can for instance be any tension as desired that reliably secures the target bone 28 without overtightening the strap 32.

Figure 4:
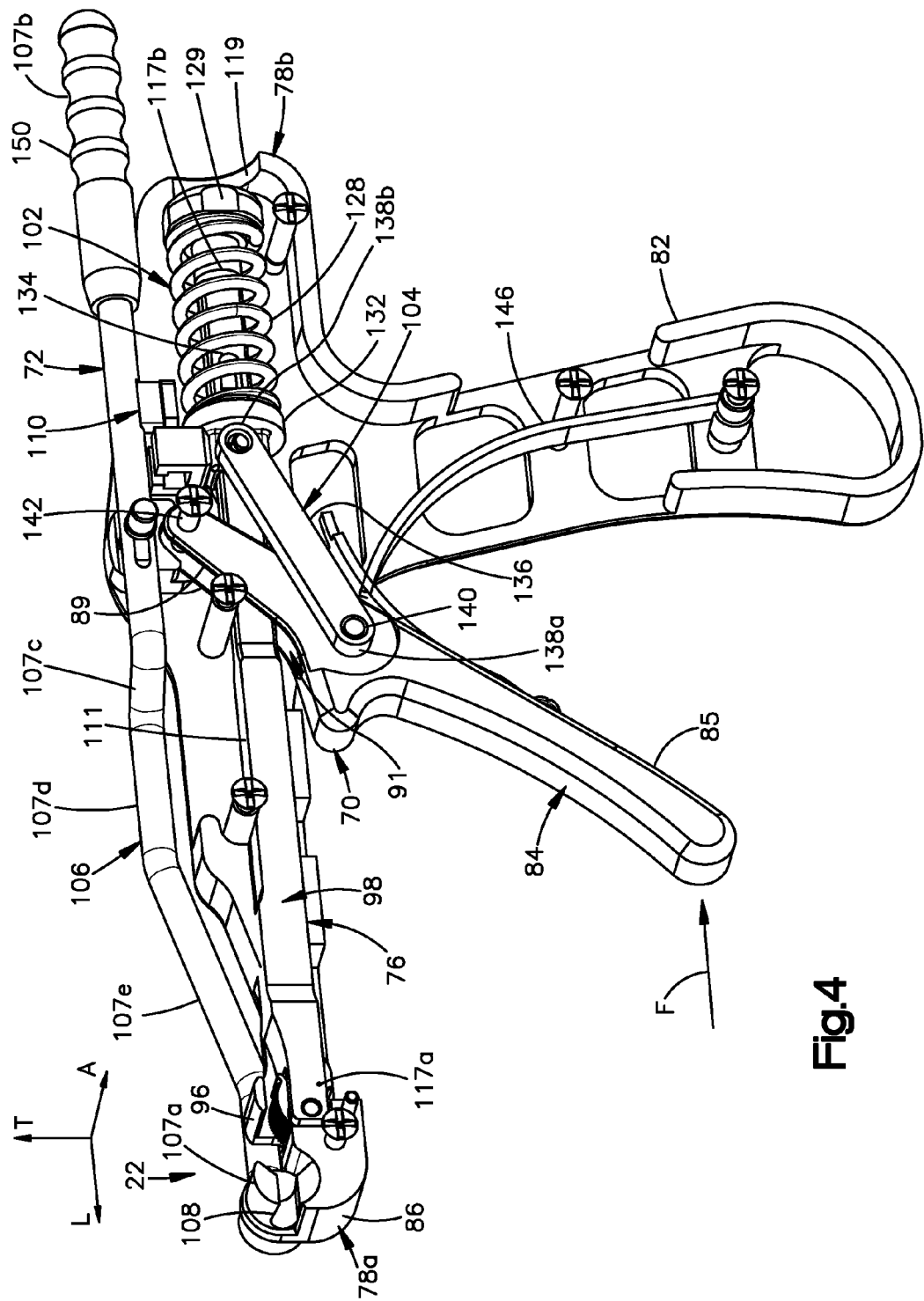
FIG. 4 is a perspective view of the bone fixation instrument illustrated in FIG. 1, with portions removed to illustrate internal components including a tension assembly and a cutter assembly.

Referring now to FIGS. 1 and 4, the fixation instrument 22 includes a body 76 that defines a front end 78a and an opposed rear end 78b spaced from the front end 78a along a longitudinal direction L and opposed sides 80 that are spaced along a lateral direction A that is substantially perpendicular with respect to the longitudinal direction L. The fixation instrument 22 further includes a handle 82 that is supported by the body 76, and can extend down from the body 76 along a transverse direction that is substantially perpendicular with respect to both the longitudinal direction L and the lateral direction A. In accordance with the illustrated embodiment, the transverse direction T is oriented vertically, and the longitudinal and lateral directions L and A are oriented horizontally, though it should be appreciated that the orientation of the fixation instrument may vary during use. In accordance with the illustrated embodiment, the body 76 is elongate in the longitudinal direction L.

The fixation instrument 22 further includes a trigger 84 that extends down from the body 76 at a location spaced forward from the handle 82, and a nose 86 disposed at the front end 78a of the body 76. The handle 82, the trigger 84, and the nose 86 can be discreetly attached to the body 76 or integral with the body 76 as desired. The body 76 can include an outer housing 88 that includes a pair of housing members 90a and 90b that are laterally opposed and define respective outer sides 92 and can be joined together via fasteners such as screws 94 so as to support the various internal components of the fixation instrument 22.

Figure 10:
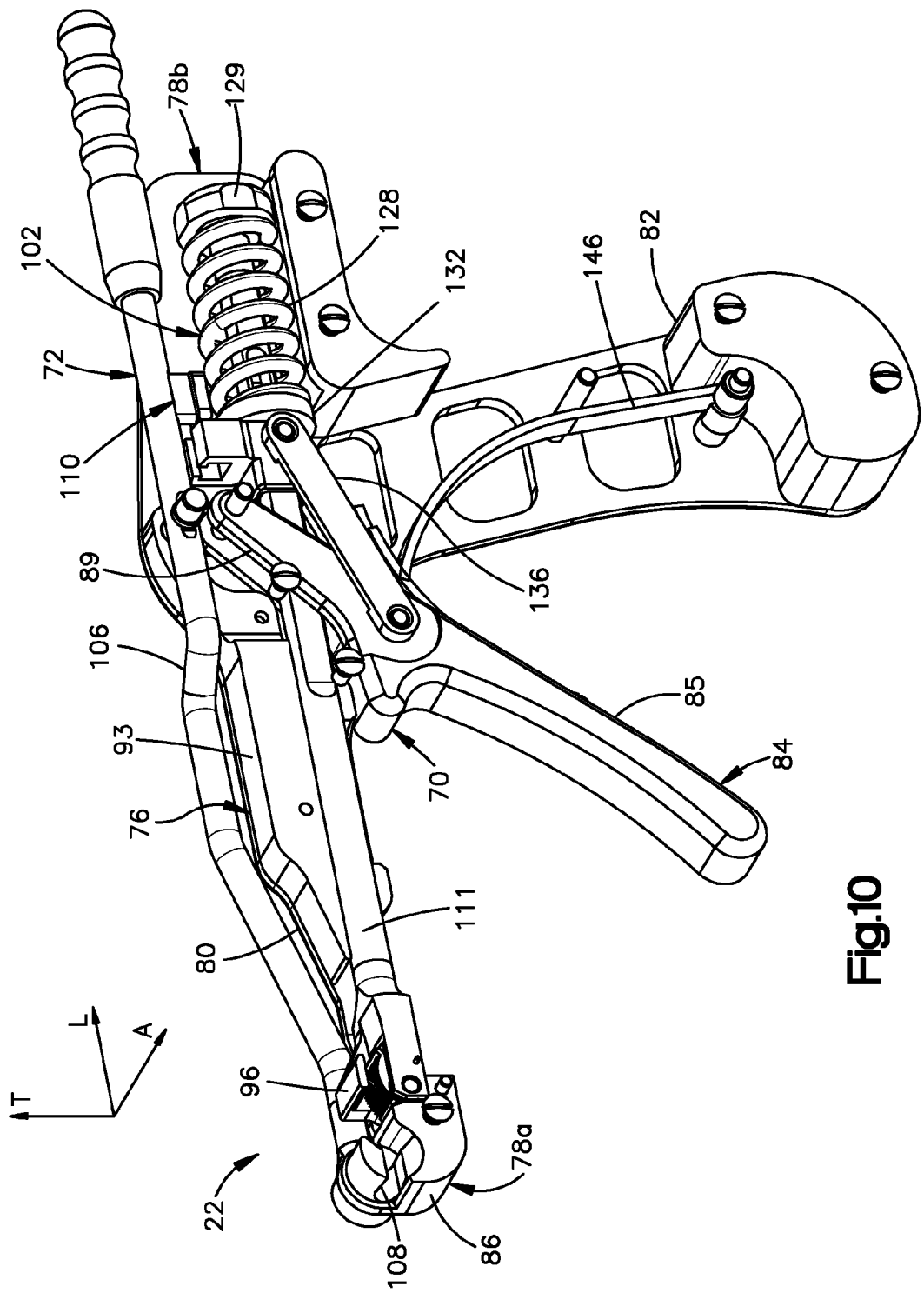
FIG. 10 is a perspective view of a bone fixation instrument similar to the bone fixation instrument illustrated in FIG. 4, but constructed in accordance with an alternative embodiment.

It should be appreciated that the body 76 of the fixation instrument 22 can be constructed in any suitable manner as desired. For instance, as illustrated in FIG. 1, the outer housing members 90a and 90b can include a flange 93 that extends laterally inward toward each other from the sides 80 at a forward location of the body 76. Alternatively, as illustrated in FIG. 10, the flange 93 can extend further rearward and terminate adjacent an actuator 100.

Furthermore, referring to FIGS. 11-15, the fixation instrument can include an outer housing 188 that can be constructed as described above with respect to the outer housing 88, or can be constructed in accordance with any suitable alternative embodiment. For instance, as illustrated in FIGS. 11-15, the outer housing 188 can include first and second housing members 190a and 190b that are spaced apart from each other along the lateral direction A. The outer housing 188 can further include at least one spacer member such as a plurality of spacer members 145, 147, and 149 that are disposed between the first and second housing members 190a and 190b. The fixation instrument 22 can further include one or more fasteners, such as screws 94, that attach the first and second housing members 190a and 190b to the spacer members 145, 147, and 149. For instance, the screws 94 can pass partially through the spacer members 145, 147, and 149, or may extend from one or both of the first and second housing members 190a and 190b, completely through the spacer members 145, 147, and 149, and all the way to the laterally opposed one of the first and second housing members 190a and 190b. The number of spacers, their respective geometric configurations, and the locations at which spacers are respectively positioned between housing members 190a and 190b may vary among different embodiments, as long as each parameter is suitable for providing adequate structural support for housing members 190a and 190b.

In accordance with the illustrated embodiment, the spacer member 145 can be disposed at a distal end of the handle 82. While the spacer member 145 is shown as a unitary part, in other embodiments the spacer 145 may be assembled, for example, from two laterally opposing halves that are mated together. Furthermore, in accordance with the illustrated embodiment, the spacer member 147 is disposed at a location that extends from the base of handle 82 rearward to along longitudinal direction L towards rear end 78b of body 76. The spacer member 147 can further include a tail 151 that is disposed at a portion of spacer 147 that is adjacent to the base of handle 82 and distal to rear end 78b of body 76, and further includes an elongate portion 153 that can extend rearward from the tail 151. The tail 151 can extend an angle that is offset from a longitudinally elongate portion 153 towards the distal end of handle 82. For example, the tail 151 can define a direction of elongation that is angularly offset from a direction of elongation of the elongate portion 153, which can be defined by the longitudinal direction L, so as to define an angle between the direction of elongation of the tail 151 and the direction of elongation of the elongate portion 153, and thus the longitudinal direction L, of approximately 85 to approximately 95 degrees. While the spacer member 147 is shown as a unitary part, it should be appreciated that the spacer member 147 may be assembled, for example, from two laterally opposing halves that are mated together.

The tail 151 and the elongate portion 153 are preferably formed from a single piece of material, but may alternatively comprise separate pieces that are bonded, welded, or otherwise fixedly attached to one another. The spacer member 149 can provide structural support for portions of the first and second housing members 190a and 190b that are located between the front end 78a and the rear end 78b of body 76. The spacer 149 can be assembled, for example, from two laterally opposing halves that are mated together during assembly of the body 76, or can alternatively be a unitary component. When the opposing halves 149a and 149b are mated together, the opposing halves 149a and 149b can define a channel 155 that extends completely through the spacer 149 along the longitudinal direction L. When the spacer member 149 comprises a unitary structure that is not assembled from two laterally opposing halves, the spacer member 149 likewise defines a channel 155 that extends completely through the spacer member 149 along the longitudinal direction L. The channel 155 can define a cross-sectional dimension, such as a diameter, that can be greater than a corresponding outer dimension of the longitudinally extending traveler 98, such that the longitudinally extending traveler 98 can move within channel 155 along the longitudinal direction L, and thus towards or away from the front end 78a and the rear end 78b, respectively, of the body 76. The fixation instrument 22 can further include at least one safety member, such as at least one corresponding wing, which can be configured as first and second laterally opposed flexible wings 161a and 161b that extend from the outer housing 188. In accordance with the illustrated embodiment, the spacer member 149 defines a first or front end 157 and an opposed second or rear end 159. As described more fully below in connection with FIGS. 11-15, the first and second wings 161a and 161b can extend from the spacer member 149, for instance at the rear end 159.

Returning to embodiments that are illustrated, for example, in FIGS. 1, 6, and 7A-B, the housing 88 can support the tension assembly 70 that is configured to tighten the bone fixation member, thereby inducing tension in the bone fixation member 24, such as the strap 32, and can further support the cutter assembly 72 that is configured to remove a free end 35 of the bone fixation member 24 once the tension assembly 70 has induced a desired level of tension in the bone fixation member 24. The tension assembly 70 includes a grip 96 that is movable between a disengaged position (FIG. 7A) whereby the grip 96 is configured to loosely receive the strap 32, such as the portion of the strap that has passed through the locking mechanism 38, and an engaged position (FIG. 7B) whereby the grip 96 is configured to be secured to the received strap 32. The tension assembly 70 further includes a traveler 98 that is operably coupled to the grip 96 and extends rearward from the grip 96, such that rearward movement of the traveler 98 causes the grip 96 to move rearward in the secured configuration, thereby inducing tension in the strap 32. The tension assembly 70 can further include an actuator 100 such as the trigger 84 and a tension limiter 102 (FIG. 6) connected between the trigger 84 and the traveler 98. The tension assembly 70 can further include a force transfer member 104 that is connected between the trigger 84 and the tension limiter 102, thereby operatively coupling the trigger 84 to the traveler 98.

During operation, and as described in more detail below, the free end 35 of the strap 32 is received in the grip 96, the nose 86 is placed against the housing 50 of the locking mechanism 38, and the actuator 100 is moved from an first initial position to a second grip position that causes the grip 96 to iterate from the disengaged position to the engaged position, and is further moved from the second grip position to a third tension position that causes the traveler 98 to move rearward, thereby inducing tension in the strap 32 when the tension in the strap 32 is less than a select tension, which can be a desired maximum tension as determined by the tension limiter 102. When the tension in the strap 32 reaches the maximum tension, the tension limiter 102 prevents the traveler 98 from moving rearward when the actuator 100 is moved to the tension position.

Figure 5A:
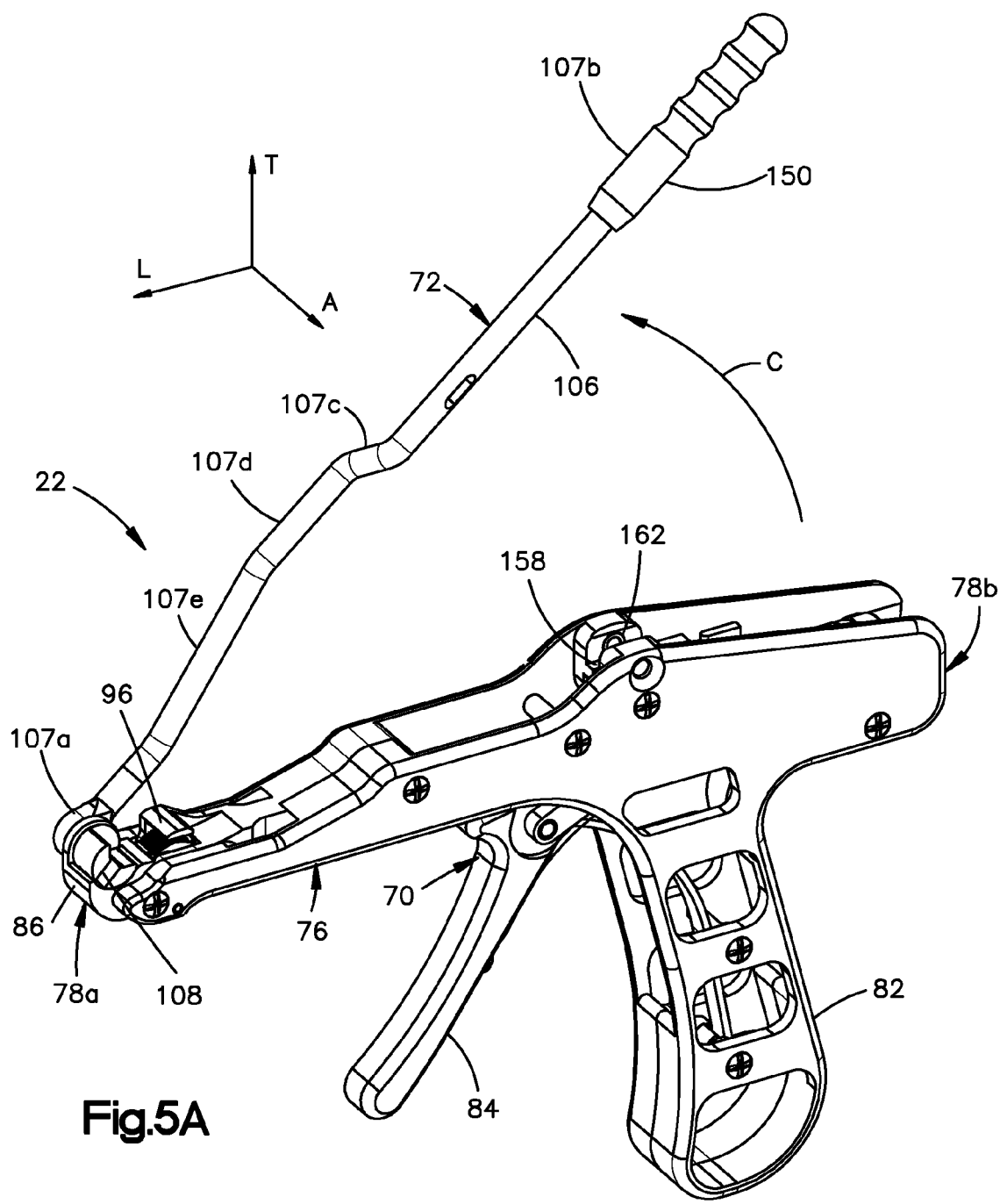
FIG. 5A is a perspective view of the bone fixation instrument illustrated in FIG. 4, showing the cutter assembly in a cutting position.
Figure 9:
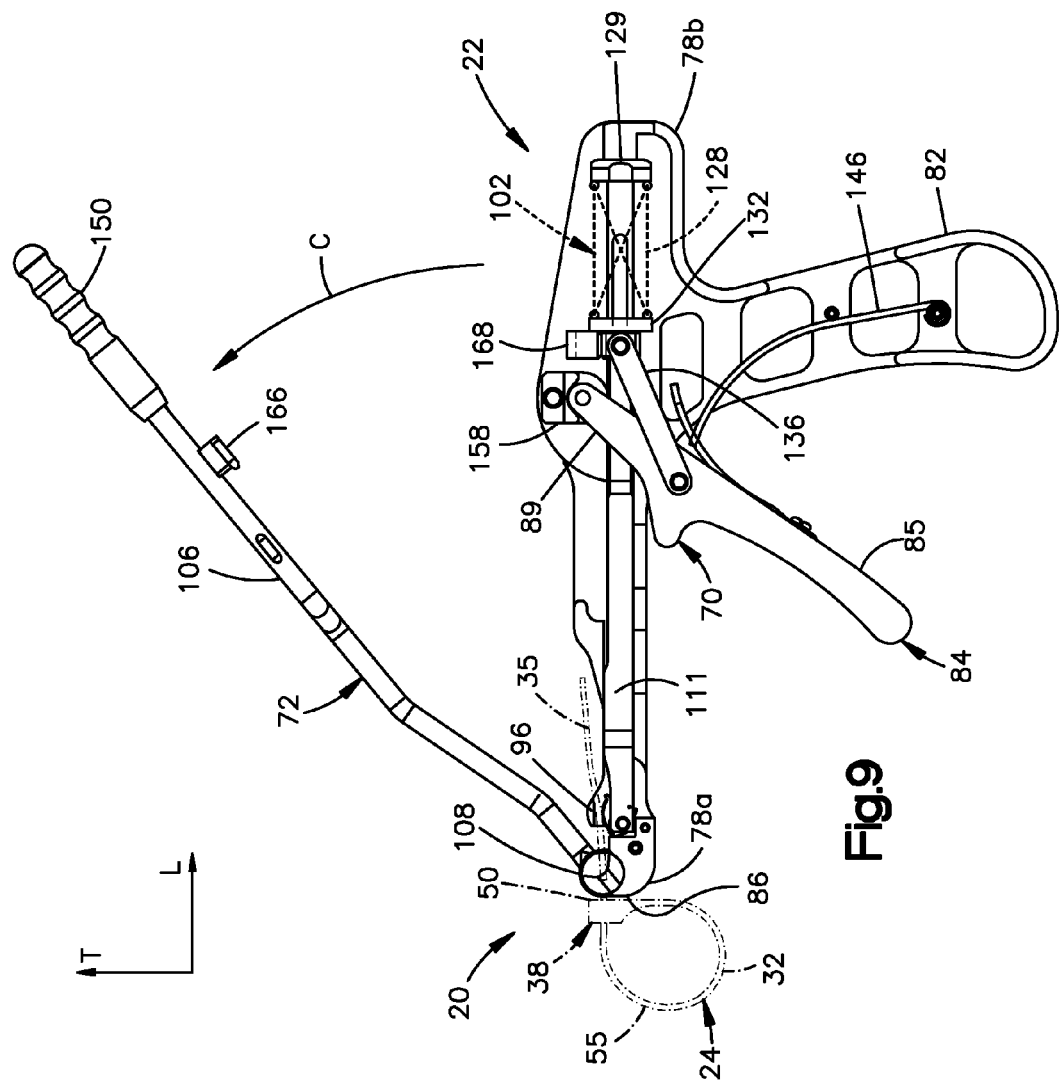
FIG. 9 is a side elevation view of the bone fixation system illustrated in FIG. 8D, but showing actuation of the cutter assembly.

The cutter assembly 72 includes a cutter arm 106 movably supported by the body 76 and a cutter blade 108 that is carried by the cutter arm 106. The cutter arm 106 is movable from a seated disengaged position (see FIG. 4) whereby the cutter blade 108 is spaced from the free end 35 of the strap 32 that is received in the grip 96 to an engaged position (see FIGS. 5A-B) whereby the cutter blade 108 cooperates with a complementary cutter blade 87 of the nose 86 so as to cut the free end 35 of the strap 32 (see FIG. 9). The fixation instrument 22, and in particular the cutter assembly 72, further includes a safety mechanism 110 that moves from a disengaged position, whereby the cutter arm 106 can move from the seated disengaged position toward the engaged position, and an engaged position that prevents the cutter arm 106 from moving from the seated disengaged position toward the engaged position.

Figure 7B:
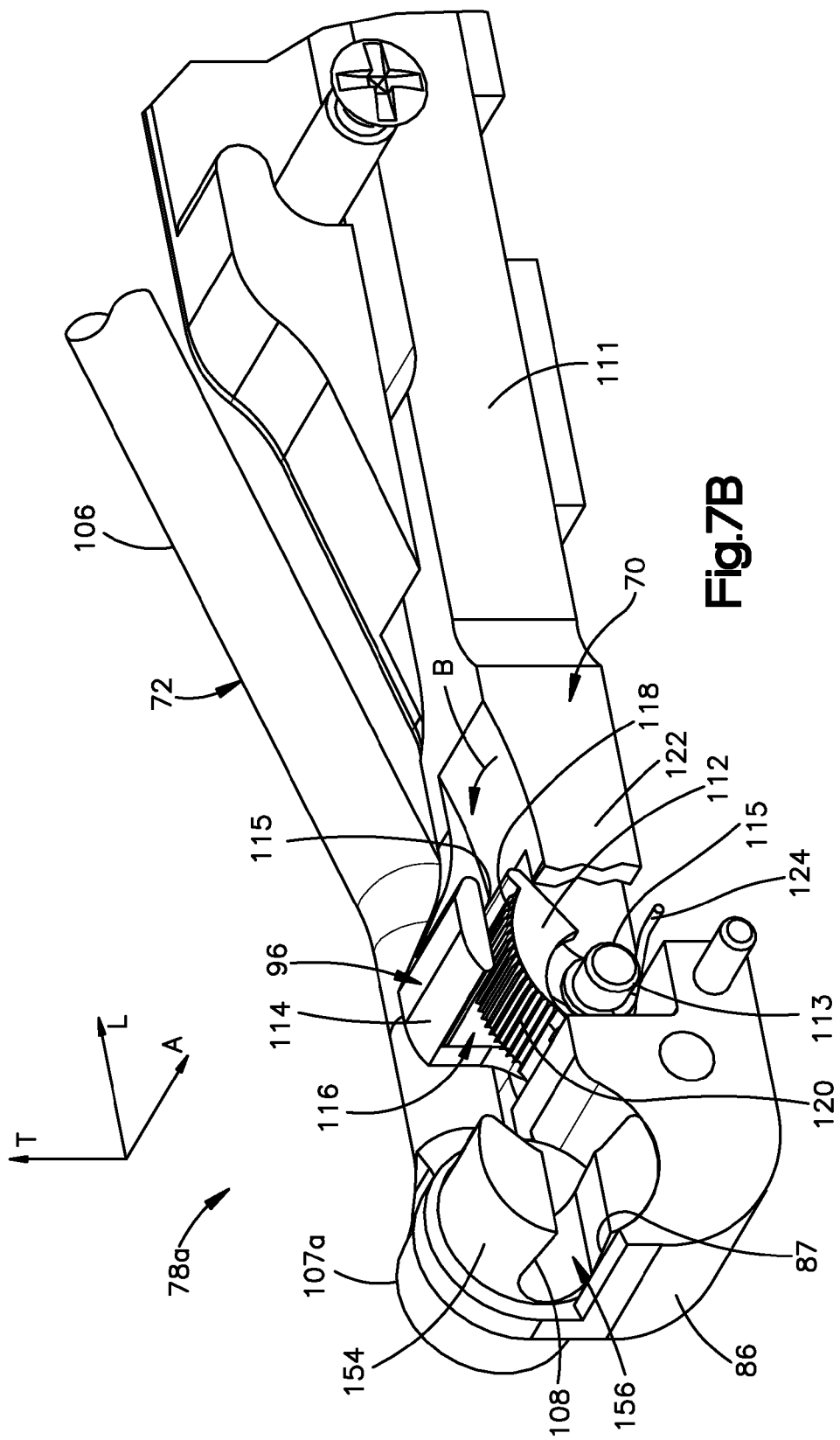
FIG. 7B is a perspective view of the distal end of the bone fixation instrument illustrated in FIG. 7A having portions removed and showing the tension assembly in an engaged position.

Referring now to FIGS. 4 and 7A-B, the traveler 98 of the fixation instrument 22 can be provided as a longitudinally extending traveler rod 111 that extends forward from the tension limiter 102 and supports the grip 96 at its front end. The traveler rod can define a rectangular cross-section as illustrated in FIG. 4, a substantially circular cross section as illustrated in FIG. 10, or any alternative size and shape as desired. The grip 96 includes a first lower grip member 112 and a second upper grip member 114 spaced from the lower grip member 112 so as to define a gap 116 disposed between the lower and upper grip members 112 and 114. The lower grip member 112 defines first grip surface 118 that faces the upper grip member 114, and can further define a plurality of teeth 120 that extend out from the first grip surface 118 toward the upper grip member 114. The teeth 120 are configured to assist in reliably securing the grip 96 to the strap 32. The upper grip member 114 is supported by the traveler rod 111 and defines a second grip surface 115 that faces the first grip surface 118. The first and second grip surfaces 118 and 115 can be sized and shaped as desired. In accordance with the illustrated embodiment, the first grip surface 118 is curved and substantially arc-shaped in accordance with the illustrated embodiment, such that the first grip surface 118 is convex with respect to the upper grip member 114. Furthermore in accordance with the illustrated embodiment, the second grip surface 115 is substantially flat.

The traveler rod 111 defines a forked first front end 117a that defines a pair of laterally spaced side walls 122. The upper grip member 114 can be rigidly supported by the traveler rod 111, and the lower grip member 112 can be pivotally coupled to the traveler rod 111 at a pivot location 113 about a laterally extending pivot pin 115 that defines a lateral pivot axis, and can further be disposed between the side walls 122. The grip 96 can further include a biasing member such as a torsion spring 124 that biases the lower grip member to pivot in a forward direction about the pivot location 113 toward the nose 86 from the disengaged position of the grip 96 to the engaged position of the grip 96. The grip surface 118 can extend eccentrically about the pivot location 113 such that the grip surface 118 moves upward toward the upper grip member 114 as the lower grip member 112 pivots forward to the engaged position.

Figure 8A:
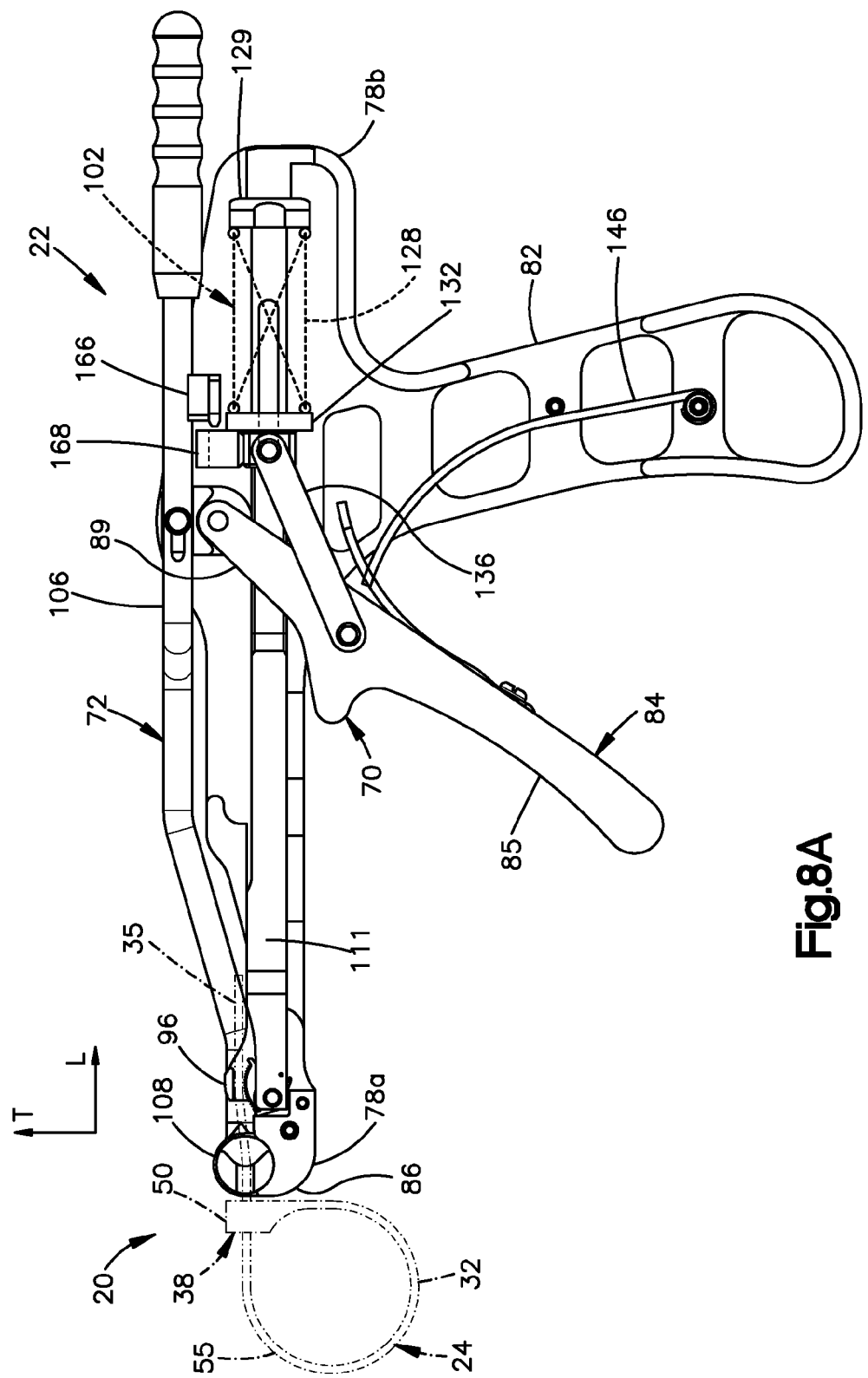
FIG. 8A is a side elevation view of the bone fixation system, including the bone fixation instrument illustrated in FIG. 4 showing the bone fixation member as illustrated in FIG. 3A, with the target bone removed for the purposes of illustration, shown loosely received in the bone fixation instrument with the tension assembly in the disengaged position.
Figure 8B:
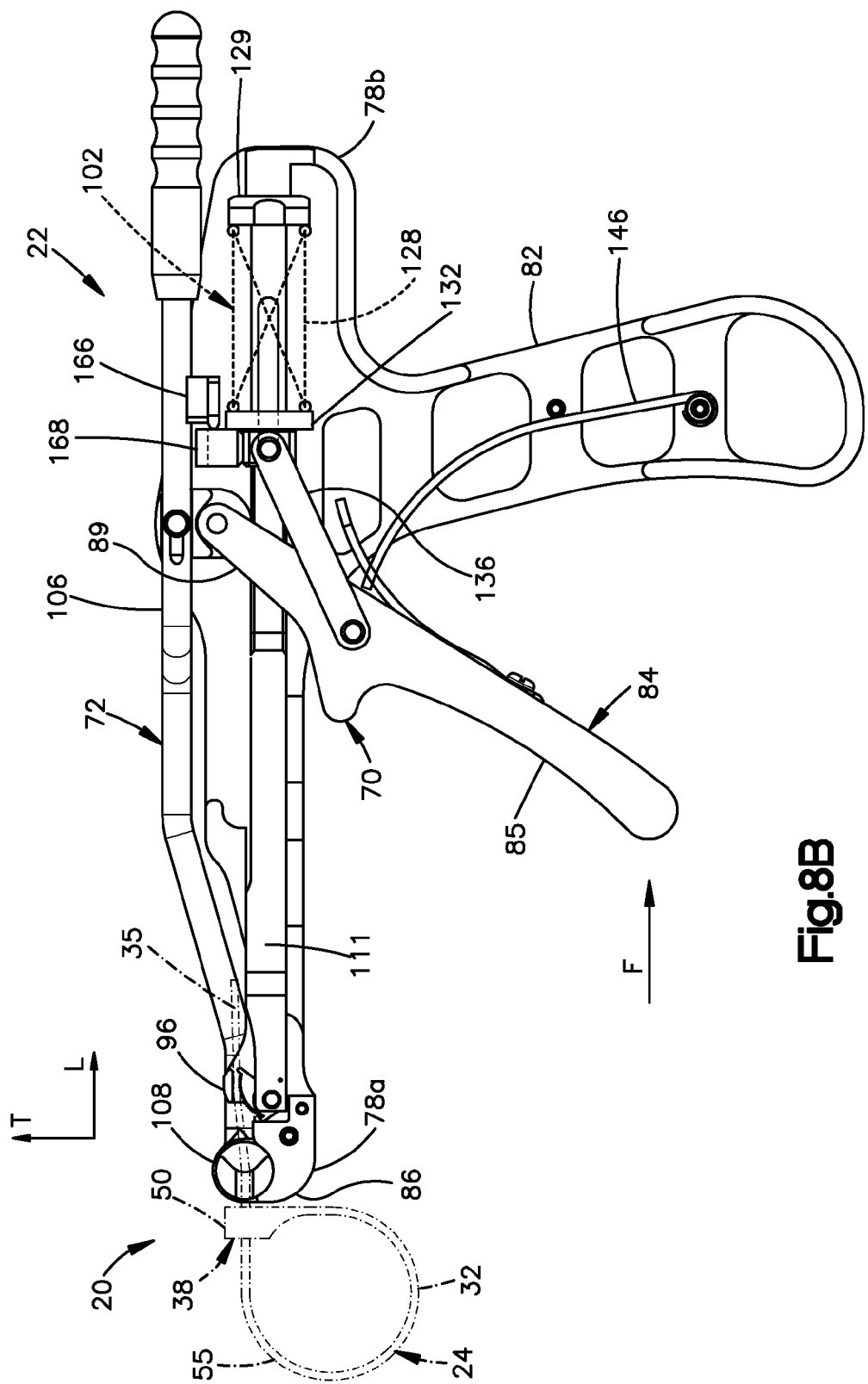
FIG. 8B is a side elevation view of the bone fixation system illustrated in FIG. 8A, showing the tension assembly in the engaged position such that the bone fixation instrument is secured to the bone fixation member.

The lower grip member 112 defines a first or forward stop surface 126 and the nose 86 defines a complementary second or rear stop surface 127. When the traveler rod 111 is in a forward position, the grip 96 is in the disengaged position whereby the torsion spring 124 biases the forward stop surface 126 against the rear stop surface 127. When the grip is in the disengaged position, the gap 116 is sized greater than the thickness of the free end 35 of the strap 32 as illustrated in FIG. 7A. Accordingly, the free end of the strap 35 can be received in the gap 116 between the first and second grip surfaces 118 and 115 as illustrated in FIG. 8A. As the traveler rod 111 moves rearward, the lower grip member 112 pivots forward about the pivot location 113 such that the grip surface 118 moves toward the grip surface 115 of the upper grip member 114 as illustrated in FIG. 7B, thereby reducing the gap 116 until the grip 95 captures the free end 35 of the strap 32 that is received in the gap 116 between the first and second grip surfaces 118 and 115 under the force of the torsion spring 124 (FIG. 8B). It should thus be appreciated that as the traveler rod 111 further moves rearward, the free end 35 of the strap 32 will move rearward along with the grip 95 and the traveler rod 111.

Figure 6:
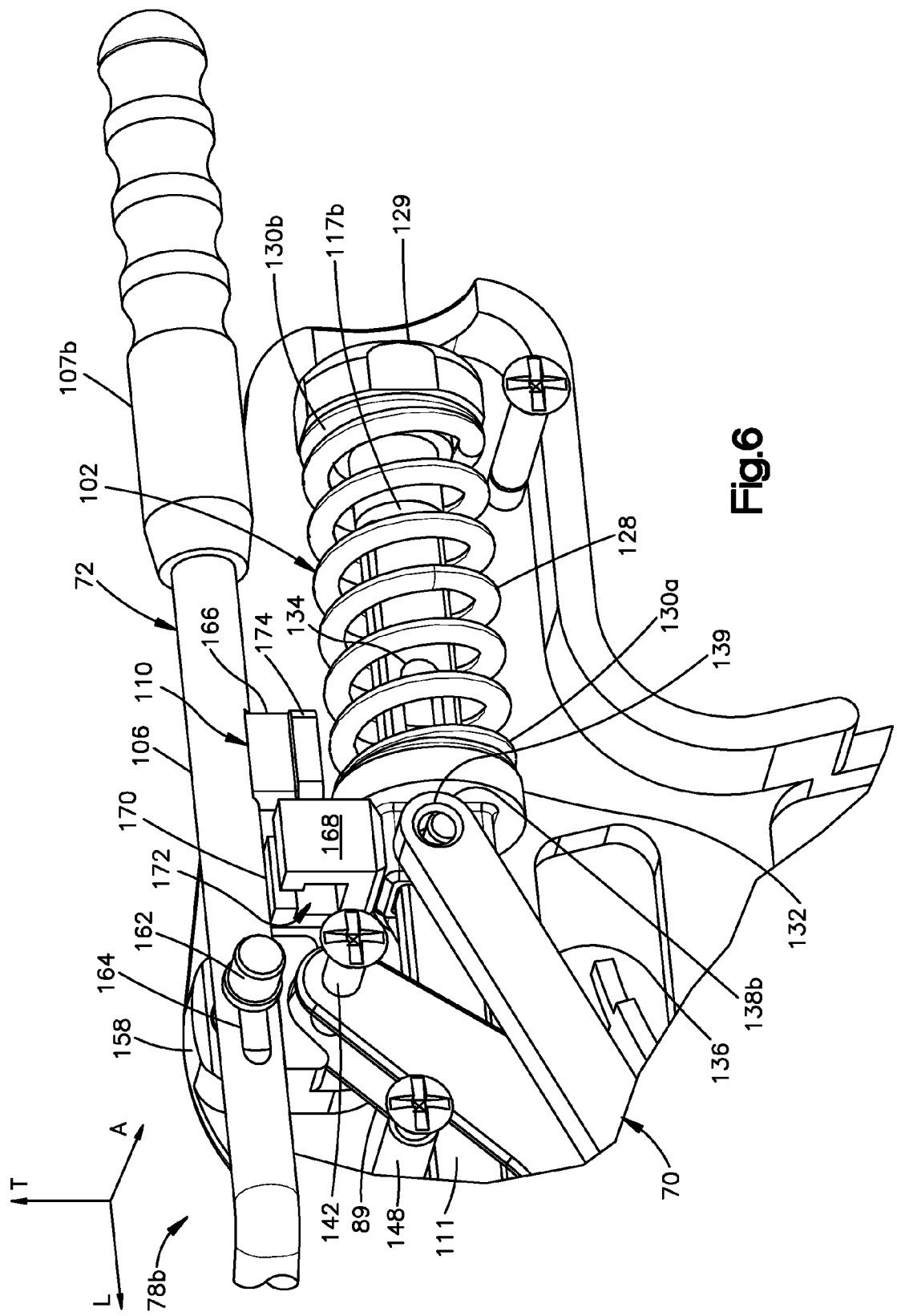
FIG. 6 is a perspective view of a rear end of the bone fixation instrument illustrated in FIG. 4.

Referring now to FIGS. 4 and 6, the traveler rod 111 defines a second rear end 117b opposite the front end 117a. The rear end 117b of the traveler rod 111 is connected to the tension limiter 102. The tension limiter 102 includes a spring member 128 such as a helical compression spring that defines a first or front end 130a and a second or rear end 130b. The spring member 128 is fixed with respect to movement relative to the traveler rod 111 at its rear end 130b, and movable with respect to the traveler rod 111 at its front end 130a. The spring member 128 is further coupled to the trigger 84 at its front end. Thus, the spring member 128 is coupled to the trigger 84 at its end that is also movable with respect to the traveler rod 111 so as to generate a force to the traveler rod 111 that biases the traveler rod rearward away from the locking mechanism 38 of the bone fixation member 24.

In accordance with the illustrated embodiment, the tension limiter 102 includes a stationary end cap 129 that can be threaded onto or otherwise secured to the traveler rod 111, for instance to the rear end 117b of the traveler rod 111. The rear end 130b of the spring member 128 is attached to the end cap 129 so as to secure the spring member 128 to the traveler rod 111 at its rear end 130b such that the rear end 130b is fixed with respect to movement relative to the rod 111. Thus, as the rear end 130b of the spring member 128 moves rearward, the traveler rod moves rearward along with the rear end 130b of the spring member 128. The tension limiter 102 can further include a movable spring seat 132 that is fixed to the movable front end 130a of the spring member 128. In accordance with the illustrated embodiment, the traveler rod 111 extends through the spring seat 132, such that the spring seat 132 is movable in the longitudinal direction L along the traveler rod 111. The traveler rod 111 can define a longitudinally elongate slot 134 extending therethrough that can receive a projection of the spring seat 132. Thus, the slot 134 defines a length that allows the movable spring seat 132 to translate from its forward-most position to its rearward-most position.

The tension assembly 70 further includes the force transfer member 104 illustrated as a force transfer arm 136 that is pivotally connected between the movable spring seat 132 and the trigger 84. Otherwise stated, the movable front end 130a of the spring member 128 is coupled to the trigger 84 via the force transfer arm 136. In accordance with the illustrated embodiment, the force transfer arm 136 defines a front end 138a and an opposed rear end 138b. The force transfer arm 136 is pivotally coupled, for instance at its rear end 138b to the spring seat 132 at a pivot location 139 that defines a lateral pivot axis. The force transfer arm 136 is further pivotally coupled, for instance at its front end 138a to the trigger 84 at a pivot location 140 that defines a lateral pivot axis.

Referring again to FIG. 4, tension assembly 70 further includes the trigger 84 that includes a lower grip portion 85 extending down from the housing 88 at a location spaced forward of the handle 82 and an upper securement portion 89 pivotally connected to the force transfer arm 136 and further pivotally connected to the housing 88. The trigger 84 defines an aperture 91 that extends longitudinally through the upper securement portion 89 and receives the traveler rod that extends through the aperture, and thus the upper securement portion 89. The securement portion 89 of the trigger 84 is pivotally connected to the force transfer arm 136 at the pivot location 140, which defines a first lower pivot location of the trigger 84. The securement portion 89 of the trigger 84 is further pivotally coupled to the housing 88 at a second upper pivot location 142 that defines a lateral pivot axis. The user can grasp the handle 82 and the grip 85 of the trigger 84 with one hand, and squeeze the trigger 84, which causes the trigger 84 to pivot rearward about the second upper pivot location 142. Because the lower pivot location 140 is disposed between the upper pivot location 142 and the grip 85, the lower pivot location 140 moves rearward when the trigger 144 is moved rearward by the user. The tension assembly 70 further includes a spring member 146 that is connected between the handle 142 and the trigger 144 that biases the trigger 144 forward to its initial position. The fixation instrument 22 includes a stop member illustrated as a dowel 148 that extends laterally between the housing members 90a and 90b. The front edge of the securement portion 89 of the trigger 84 abuts the dowel 148 so as to locate the trigger 144 in its first initial position under the force of the spring member 146.

Operation of the fixation instrument will now be described with further reference to FIGS. 8A-E. For instance, as illustrated in FIGS. 7A and 8A, the trigger 84, and thus the tension assembly 70, is in a first initial position whereby the front end 117a of the traveler rod 111 is disposed adjacent and proximate to the nose 86, such that the forward stop surface 126 of the lower grip member 112 abuts the complementary rear stop surface 127 of the nose 86, thereby causing the gap 116 to define a transverse thickness greater than that of the free end 35 of the strap 32. The free end 35 is inserted into the gap 116 and the nose 86 is positioned so as to abut the locking mechanism 38. The nose 86 thus provides a brace member that prevents the locking mechanism 38 from traveling rearward when the fixation instrument 22 applies a rearward force to the free end 35.

When the tension assembly 70 is in the first initial position, the spring member 128 can be in an initial position that can be a neutral position, or the movable spring seat 132 can be disposed at a forward location with respect to the neutral position such that the initial position of the spring member 128 can be flexed, such as slightly extended, from its neutral position. For instance, the force of the spring member 146 that biases the trigger 84 forward can be greater than the force of the spring member 128 that biases the trigger 84 rearward when the movable spring seat 132 is displaced forward from its neutral position. When the spring member 128 is extended from its neutral position, the spring member can apply a rearward compressive force onto the end cap 129, and thus the traveler rod 111, which biases the lower grip member 112 forward against the nose 86. It is appreciated that the torsion spring 124 that biases the lower grip member 112 forward against the nose 86 creates an equal and opposite force against the traveler rod 111 that biases the traveler rod rearwards. Thus, the forward force of the spring member 128 applied to the traveler rod 111 when the spring member 128 is slightly extended is greater than the rearward biasing force of the torsion spring 124 against the traveler rod 111. Because the forward biasing force of the spring member 128 is greater than the rearward biasing force of the torsion spring 124 when the spring member 128 is slightly extended, the spring member 128 can actively maintaining the grip 96 in its disengaged position.

Alternatively, the movable spring seat 132, and thus, the spring member 128, can be in a neutral position when the tension assembly 70 is in the first initial position, such that the spring member 128 does not apply a forward biasing force or a rearward biasing force to the traveler rod 111. As described above, the torsion spring 124 can apply a force to the traveler rod 111 that biases the traveler rod rearwards 111. However, rearward movement of the traveler rod 111 would cause the rear end 130b of the spring member 128 to move away from the front end 130a of the spring member 128, thereby causing the spring member 128 extend from its neutral position. The spring member 128 can have an spring constant that is greater than the spring constant of the torsion spring 124 such that the spring member 128 resists extension under the forces of the torsion spring 124, and thereby passively maintains the lower grip member 112 in its disengaged position whereby the forward stop surface 126 rests against the complementary rear stop surface 127 of the nose 86 and the gap 116 is thus thicker in the transverse direction T than the free end 35 of the strap 32 that is received in the gap 116.

Referring now to FIGS. 4 and 8B, when the user applies an actuation force, such as a rearwardly directed force F, to grip portion 85 of the trigger 84, the trigger 85 and thus also the tension assembly 70 moves from the first initial position to the second grip position that causes the grip 96 to iterate from the disengaged position to the engaged position. In accordance with the illustrated embodiment, the rearward force applied to the grip portion 85 of the trigger 84 causes the trigger 84 to pivot rearward about the upper pivot location 142, which causes the lower pivot location 140 to move rearward. It should be appreciated that the lower pivot location 140 moves rearward about an arc-shaped travel path about the upper pivot location 142. Rearward movement of the lower pivot location 140 causes the force transfer arm 136 to likewise moves rearward, thereby transferring the force from the trigger to the movable spring seat 132 and the front end 130a of the spring member 128. It should be appreciated that the force transfer arm 136 pivots relative to the trigger 84 about the lower pivot location 140 as the force transfer arm 136 moves rearward.

As the force transfer arm 136 moves rearward, the force transfer arm 136 further causes the movable spring seat 132 and the front end 130a of the spring member 128 to translate rearward along the travel rod 111 in the longitudinal direction L toward the rear end 130b of the spring member 128, thereby flexing the spring member 128 from the first initial position. It should be appreciated that the force transfer arm 136 pivots relative to the movable spring seat 132 about the pivot location 139. As the front end 130a of the spring member 128 moves rearward toward the rear end 130b of the spring member 128, the spring member 128 flexes from its neutral position so as to apply a rearward biasing force to the traveler rod 111. In accordance with the illustrated embodiment, the spring member 128 compresses when the end 130a of the spring member 128 moves rearward, and thus biases the end 130b, the end cap 129, and also therefore the traveler rod 111 to move rearward. Alternatively, the movement of the end 130a of the spring member 128 can be sufficient so as to reduce the force of the spring 128 that biases the traveler rod 111 to a level that is less than the force of the torsion spring 124 that biases the traveler rod 111 rearward. The fixation instrument 22 can define an aperture 119 that extends through the rear end 78b of the body 76. The aperture 119 is sized to receive the end cap 129 such that the end cap 129 can extend beyond the housing 88 due to rearward travel of the rear end 130b of the spring member 128.

Accordingly, referring also to FIGS. 7A-B, the traveler rod 111 is biased, under a biasing force applied by the torsion spring 124, the spring member 128, or both to move rearward away from the nose 86. As the rod 111 moves away from the nose 86, the torsion force of the torsion spring 124 causes the lower grip member 112 to pivot forward about the pivot location 113 along the direction of Arrow B so as to reduce the gap 116 until the grip surfaces 118 and 115 capture the free end 35 of the strap 32 in the gap 116, thereby securing the free end 35 to the fixation instrument 22 while the nose 86 abuts the loop 55, and in particular the housing 50 of the locking mechanism 38. Thus, it can be said that moving the trigger 84 from the first neutral position to the second neutral position causes the grip 96 to iterate from its disengaged position to its engaged position.

Figure 8C:
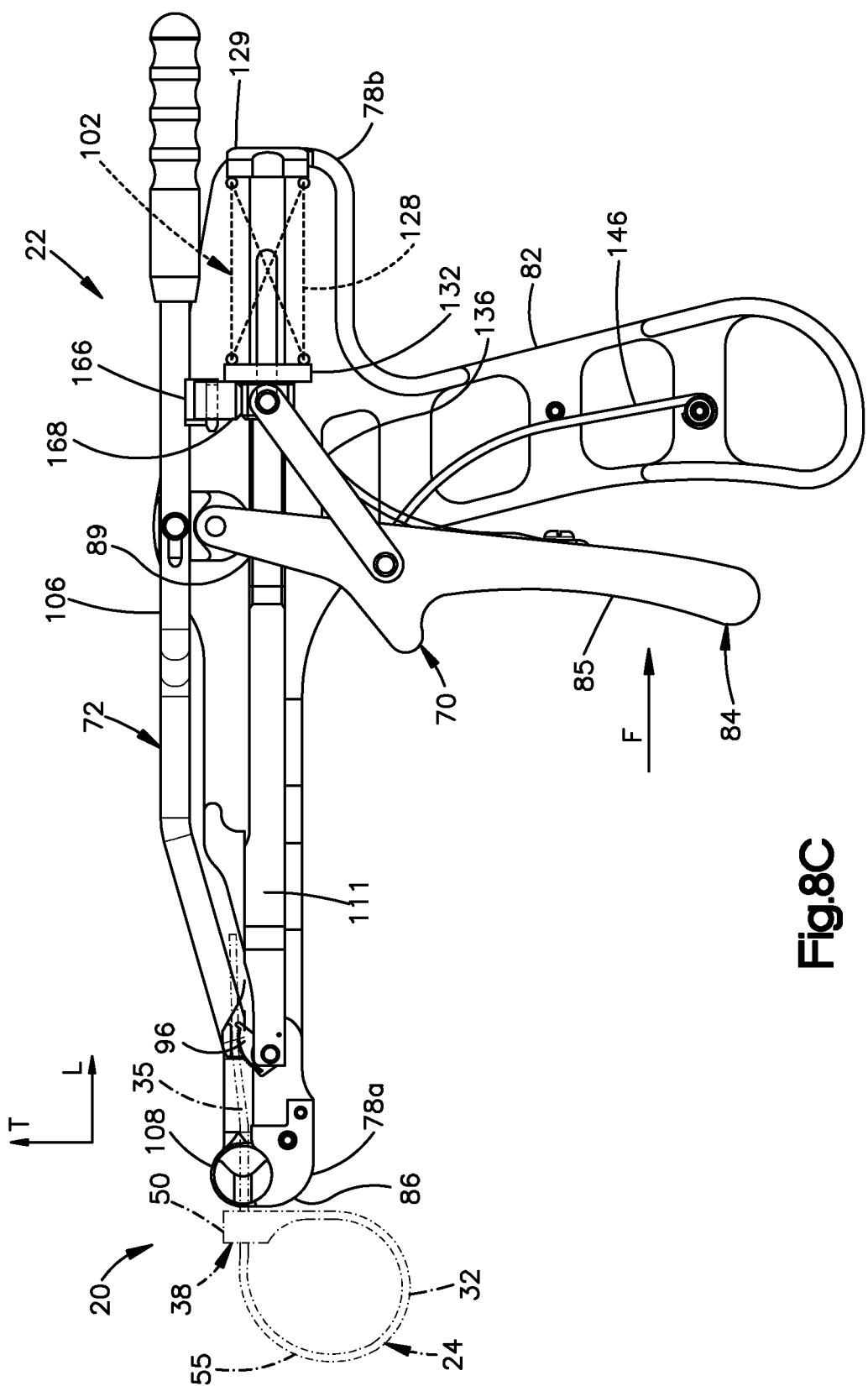
FIG. 8C is a side elevation view of the bone fixation system illustrated in FIG. 8B, showing the tension assembly in a tightened position.

Referring now to FIGS. 4, 6, and 8C, continuous application of the force F to the grip portion 85 of the trigger 84 causes the trigger 84 to further pivot about the upper pivot location 142, thereby causing the trigger 84, and thus the tension assembly 70, to move from the second grip position to a third tension position that causes the traveler 98 to move rearward, thereby applying tension to the free end 35 of the strap 32 when the tension in the strap 32 is less than the desired tension, such as a maximum tension as determined by the tension limiter 102. Because engagement of the nose 86 of the fixation instrument 22 with the loop 55, and in particular the housing 50 of the locking mechanism 38, provides a brace that prevents the loop 55 from moving rearward along with the free end 35, when the tension assembly 70 places the free end 35 in tension, the strap 32 and in particular the locking region 42 is further pulled through the locking mechanism 38. As described above with reference to FIG. 2B, the locking teeth 58 and 48 engage so as to allow the locking region 42 to be pulled through the locking mechanism so as to reduce the size of the loop 55 or to place the loop 55 in further tension about the bone segments that are disposed in the loop 55. Whether the size of the loop 55 is reduced or whether the loop 55 is further tightened about the bone segments disposed in the loop, it can be said that the fixation instrument places the bone fixation member 24 in tension when the tension assembly moves from the second grip position to the third tension position.

Figure 8D:
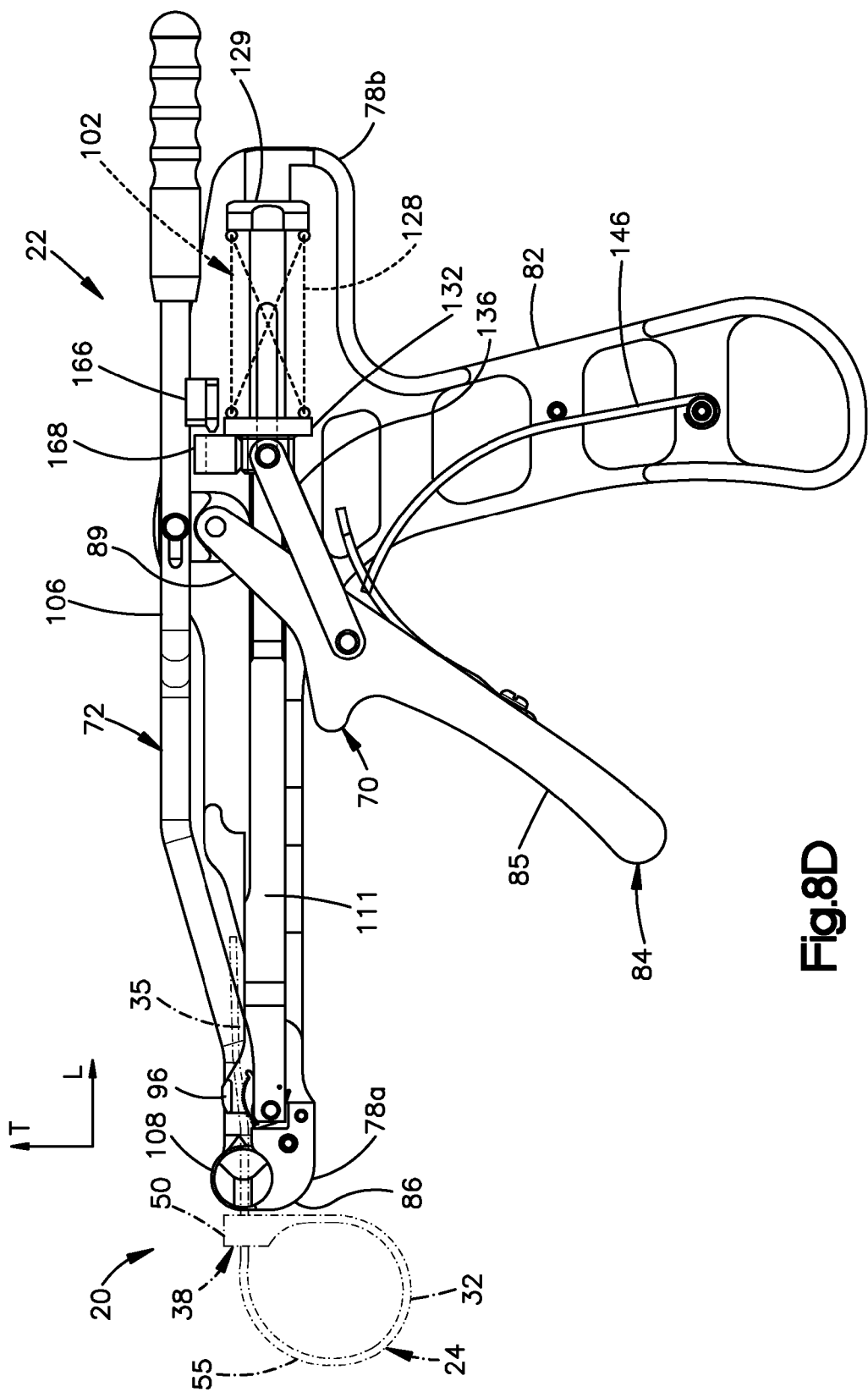
FIG. 8D is a side elevation view of the bone fixation system illustrated in FIG. 8C, showing the tension assembly in a disengaged position after having been previously in the tightening position FIG. 8C.

Accordingly, once a trigger stroke has been completed whereby the trigger 84 has been moved to its rearward-most position as illustrated in FIG. 8C, the user can release the trigger 84 which causes the spring member 146 to bias the trigger 84 to its forward position shown in FIG. 8D. Once the trigger 84 has moved to its forward position, the trigger 84 and thus the tension assembly 70 are in the first initial position, such that the lower grip member 112 is biased against the nose 86 thereby placing the grip 96 in its disengaged position as described above. Accordingly, while the free end 35 of the strap 32 is no longer secured to the fixation instrument 22, the engagement of the locking teeth 58 and 48 prevent the increased tension induced in the loop 55 from allowing the free end 35 to move through the housing in a direction opposite Arrow A that would reduce the tension in the loop 55.

It should be appreciated that the motion of the trigger 84 from the second grip position to the third tension position can be a continuation of the movement from the first initial position to the second grip position. Thus, the trigger 84 can move from the first initial position to the second grip position to the third tension position in a single fluid motion.

The nose 86 can again be placed in contact with the locking mechanism 38 and the free end 35 can be received in the gap 116 of the grip 96, and the tension assembly 70 can be iterated from the first initial position to the second grip position to the third tension position as many times as desired, for instance until the tension induced in the loop 55 reaches a predetermined maximum tension. When the tension in the loop 55 reaches the maximum tension, the tension limiter 102 prevents the traveler 98 from moving rearward when the actuator 100 is moved to the tension position.

Figure 8E:
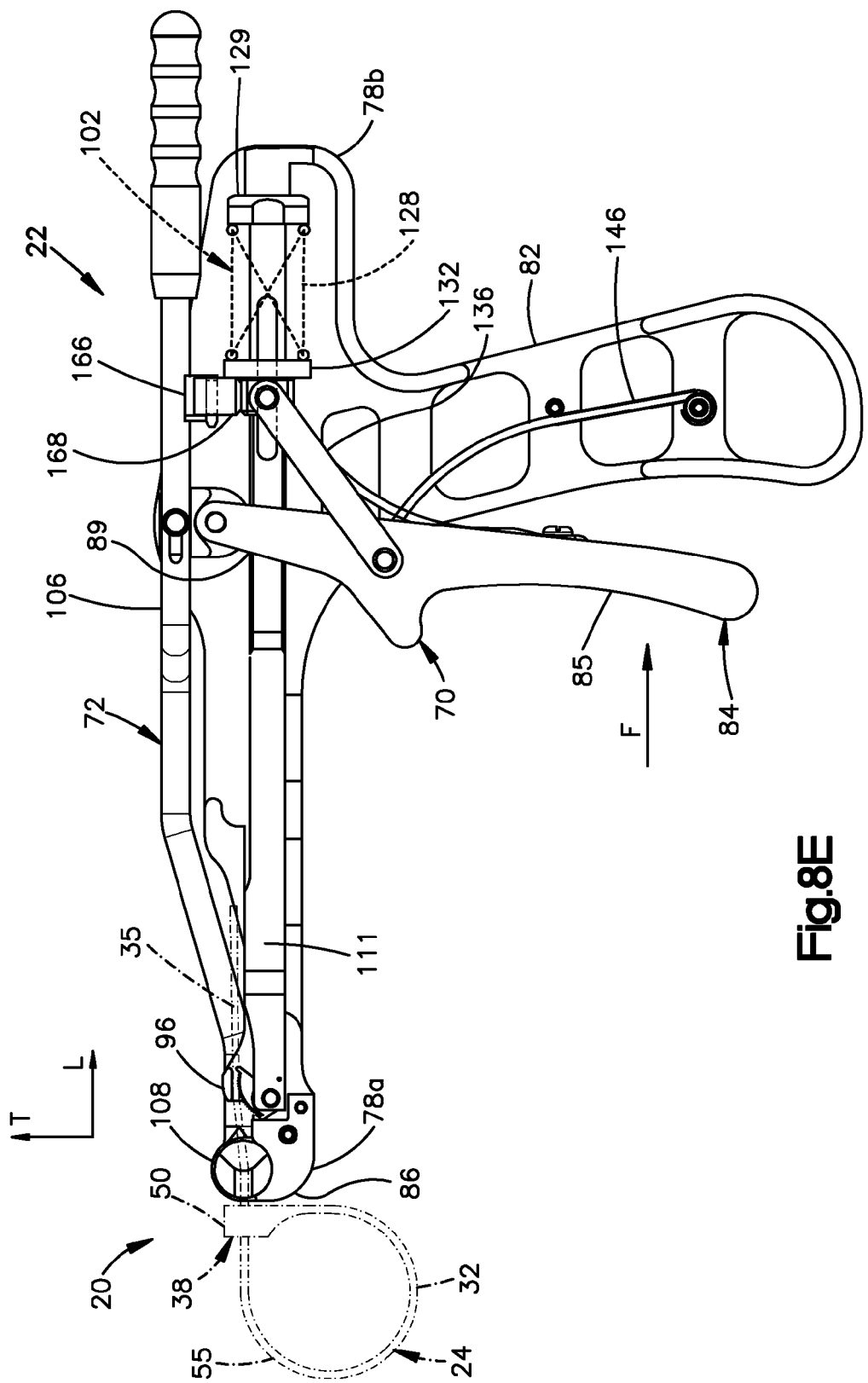
FIG. 8E is a side elevation view of the bone fixation system illustrated in FIG. 8D, showing the operation of a tension limiter whereby actuation of the tension assembly toward the tightened position does not tighten the received bone fixation member.

For instance, referring now to FIGS. 4, 6, and 8E, it should be appreciated that the spring member 128 has a spring constant that is configured to apply a predetermined biasing force to the traveler rod 111 when the front end 130a of the spring member 128 has translated rearward a distance corresponding to full rearward actuation of the trigger 84. Accordingly, so long as the tension in the loop 55 is less than the desired force as defined by the spring member 128 and length of travel of the front end 130a of the spring member 128, compression of the spring member 128 will cause the force applied by the spring member 128 to move the traveler rod 111 rearwards. However, once the tension induced in the loop 55 reaches the desired force, compression of the spring member 128 due to rearward movement of the front end 130a will cause the spring member 128 to apply a rearward biasing force against the traveler rod 111 that is insufficient to overcome the force necessary to further tighten the loop 55.

It should appreciated that the spring member 128 can be configured to apply a rearward biasing force against the traveler rod 111 that is greater than the tension induced in the loop 50 about the target bone 28. For instance, the spring member 128 can apply a force that is sufficient to overcome both the tension of the loop 50 and the additional force that causes one or both of the locking teeth 48 and 52 to deflect as the teeth ride over each other when tightening the loop 55. Accordingly, the tension limiter 102 can be configured apply a force that is greater than, but corresponds to, the tension in the loop 55 about the target bone. Thus, the maximum force applied by the tension limiter 102 can correspond to the maximum desired tension in the loop 55, it being appreciated that once the teeth 48 and 52 ride over and past each other, the tension in the loop 55 can decrease somewhat as the teeth 48 and 52 interlock. In accordance with one embodiment, the tension limiter 102 can apply a maximum force as desired, for instance up to approximately 430 Newtons or any other force as desired that corresponds to a desired maximum tension in the loop 55 about the target bone 28. As a result, once the desired maximum tension in the loop 55 has been induced about the target bone 28, the force applied by the tension limiter 102 when the trigger 84 is fully actuated is insufficient to cause the teeth 48 and 58 to ride past each other and further tighten the loop 55. Accordingly, once the maximum tension in the loop 55 has been induced about the target bone 28, the force applied by the tension limiter 102 will be insufficient to cause the traveler rod 111 to translate rearward a sufficient distance that further tightens the loop 55 about the target bone 28.

It should be appreciated that the spring member 128 can alternatively be configured as an extension spring. For example, in accordance with an alternative embodiment, the front end 130a can be connected to the traveler rod 111 and fixed with respect to the traveler rod 111, and the rear end 130b can be movable relative to the traveler rod 111. For instance, the rear end 130b can be coupled to the trigger 84 via the force transfer member 104 in the manner described above. The tensile force applied to the rear end 130b and corresponding rearward displacement of the rear end 130b can thus cause the spring force to bias the traveler rod 111 to move rearward, thereby inducing tension in the strap 32 in the manner described above. Thus, the initial position of the spring member 128 initial position that can be a neutral position as described above, or the initial position of the spring member 128 can be flexed, such as slightly compressed, from its neutral position.

Referring now to FIGS. 4-5B, the fixation device 22 includes a cutter assembly 72 that includes a cutter arm 106 having a front end 107a and a rear end 107b, and a movable cutter blade 108 carried by the cutter arm 106, for instance at the front end 107a. The cutter arm 106 can be sized and shaped as desired, and is constructed in accordance with the illustrated embodiment such that the front and rear ends 107a and 107b extend substantially longitudinally. The cutter arm 106 can also include an offset segment 107c that extends laterally outward along a forward direction from the rear end 107b toward the front 107a. Thus, the front end 107a can be offset laterally outward with respect to the rear end 107b. For instance, the rear end 107b can be disposed between the opposed sides 80 and the front end 107a can be coupled to one of the side 80 at a location laterally outward of the side 80. The cutter arm 106 can further include an intermediate longitudinal segment 107d that extends forward from the offset segment 107c and is thus extends substantially parallel to the front and rear ends 107a and 107b. The cutter arm can also include a transversely offset segment 107e that extends between the intermediate longitudinal segment 107d and the front end 107a, and extends transversely down along a forward direction. Accordingly, the front end 107a can be transversely offset with respect to the rear end 107b. The cutter arm 106 can further include a grip 150 at disposed at the rear end 107b.

Referring also to FIG. 6, the cutter assembly 72 can include a seat 158 that receives the cutter arm 106 at an upper end of the body 76 when the cutter arm 106 is in its disengaged position. In accordance with the illustrated embodiment, the seat 158 is sized and shaped so as to receive the cutter arm 106. Accordingly, when the cutter arm 106 is seated in the seat 158, the cutter arm 106 can be said to be in a seated disengaged position. The seat 158 can further include at least one retainer member 162, such as a pair of laterally opposed retainer members 162 that are spaced apart a distance slightly less than the lateral thickness of the cutter arm 106. The retainer members 162 can be spring loaded to the position spaced apart a distance slightly less than the lateral thickness of the cutter arm 106. For instance, the cutter arm 106 can define a recess 164 that is sized to receive the retainer members 162 when the cutter arm 106 is in its seated disengaged position. Accordingly, when moving the cutter arm 106 to and from its seated disengaged position, an engagement force along the direction of Arrow C can be applied to the cutter arm 106 that is sufficient to overcome the retention force of the retainer members 162, which causes the retainer members 162 to pop out of the recess 164 and free the cutter arm 106 from the seat 158.

Referring also to FIGS. 7A-B, the cutter arm 106 can be pivotally attached to the body 76, for instance at one of the sides 80. In accordance with the illustrated embodiment, the cutter arm 106 is pivotally attached at its front end 107a to the nose 86 at a pivot location 152 that defines a lateral pivot axis. For instance, the cutter assembly 72 can include a blade support body 154 that is substantially cylindrical and extends through a side wall of the nose 86 and rotatable about its central axis so as to allow the cutter arm 106 to pivot between its engaged position and its disengaged position. When the cutter arm 106 is in its disengaged position, the cutter blade 108 is spaced above a complementary and substantially stationary cutter blade 87 of the nose 86 so as to define a gap 156 that has a transverse dimension greater than that of the free end 35 of the strap 32 so that the free end 35 is loosely received in the gap 156, which is disposed forward with respect to the grip 96, and thus the gap 116.

Referring again to FIGS. 5A-B, the cutter arm 106 can be pivoted up and forward about the pivot location 152 along the direction of Arrow C to its engaged position, which causes the cutter blade 108 to travel down along an arc-shaped path toward the complementary cutter blade 87 so as to reduce the size of the gap 156. The cutter blade 108 is recessed rearward with respect to the complementary cutter blade 87 such that the cutter blade 108 slides past the cutter blade 87. Accordingly, the cutter blades 108 and 87 cooperate so as to cut the free end 35 of the strap 102 that is received in the gap 156 as the cutter blade 108 slides past the cutter blade 87 (see FIG. 9). Accordingly, when the nose 86 abuts the locking mechanism 38 of the bone fixation member 24 such that the gap 156 is aligned with the outlet end of the strap-receiving slot 52 of the housing 50 of the locking mechanism (see FIGS. 2B and 3C) and the arm 106 is moved to its engaged position, the cutter assembly 72 can cut the free end 35 at a location that is spaced from the housing 50 a distance substantially equal to the distance between the front end of the nose 86 and the cutter blade 108. Therefore, once the fixation instrument 22 has applied the desired amount of tension in the strap 32, the free end 35 can be cut in the manner described above to substantially remove the free end 35 from the loop 55.

Referring now to FIGS. 4 and 6, the cutter assembly 72 further includes a safety mechanism 110 that moves from a disengaged position, whereby the cutter arm 106 can move from the seated disengaged position toward the engaged position, and an engaged position that prevents the cutter arm 106 from moving from the seated disengaged position toward the engaged position. In accordance with the illustrated embodiment, the cutter assembly 72 includes a first engagement member 166 that extends down from the cutter arm 106 and a second engagement member 168 that extends up from the movable spring seat 132. When the tension assembly 70 is in the first initial position, the first engagement member 166 is spaced rearward from the movable spring seat 132. Otherwise stated, the first engagement member 166 is spaced from the movable spring seat 132 in the direction that the spring seat 132 moves when the tension assembly 70 is moved from the first initial position toward the third tension position. Accordingly, second engagement member 168 can move toward the first engagement member as the movable spring seat 132 moves rearward. Alternatively, the second engagement member 168 can extend from the traveler rod 111 and movable along with the traveler rod 111 so as to interlock with the engagement member 166.

The first and second engagement members 166 and 168 are configured so as to interlock when they longitudinally overlap. For instance, the second engagement member 168 can be configured as a housing 170 having a slot 172 that receives the first engagement member 166. The first engagement member 166 can define a flange 174 that overlaps the housing 170 in the transverse direction, such that the flange 174 abuts the housing 170 when an engagement force is applied to the cutter arm 106 along the direction of Arrow C so as to move the cutter arm 106 from its seated disengaged position toward its engaged position. In accordance with the illustrated embodiment, the first and second engagement members 166 and 168 interfere so as to prevent the cutter arm 106 from being unseated from the seat 158. It should be appreciated that the first engagement members 166 and 168 can alternatively be sized and shaped as desired so as to selectively interfere with each other in the manner described herein.

Referring also to FIG. 8A, when the tension assembly 70 is in the first initial position, the first and second engagement members 166 and 168 are longitudinally spaced apart such that the cutter arm 106 can be moved from the seated disengaged position to the engaged position along the direction of Arrow C. When the tension assembly 70 moves to the second grip position, the movable spring seat 132 translates longitudinally rearward, thereby also translating the second engagement member 168 longitudinally rearward toward the first engagement member 166. In accordance with the illustrated embodiment illustrated in FIG. 8B, the engagement members 166 and 168 remain longitudinally spaced from each other when the tension assembly 70 is in the second grip position, thereby allowing the cutter arm 106 to become unseated and move from the disengaged position toward the engaged position. Accordingly, referring to FIG. 9, after the fixation instrument 22 has induced a desired amount of tension in the loop 55, the tension assembly 70 can be moved to the grip position so as to capture the free end 35 in the gap 116 prior to cutting the free end 35 in the manner described above. Thus, as illustrated in FIG. 3A, the plurality of bone fixation members 24 can be tightened about the target bone 28 by actuating the tension assembly 70 as described herein, and can be subsequently cut by actuating the cutter assembly 72 as described herein.

In accordance with the illustrated embodiment shown in FIG. 8C, the engagement members 166 and 168 are positioned so as to overlap when the tension assembly 70 has moved from the second grip position toward the third tension position. Thus, once the tension assembly 70 has advanced beyond the second grip position, the engagement members 166 and 168 interfere when the engagement force is applied to the cutter arm 106 along the direction of Arrow C. Therefore, the safety mechanism 110 prevents the fixation instrument 22 from cutting the free end 35 while the tension assembly 70 is applying tension to the strap 32. Alternatively, the engagement members 166 and 168 can be positioned so as to at least partially overlap and interlock when the tension assembly 70 is in the second grip position, thereby defining an interference that prevents the cutter arm 106 from becoming unseated and moving to the engagement position along the direction of Arrow C.

Referring now to FIGS. 11-15, the fixation instrument 22 can include the safety mechanism 110, that in turn includes first engagement member 166 and second engagement member 168 (the interaction of which is described in detail above), and can further include a second safety mechanism 195 that prevents the tension assembly 70 from moving to the tightened position while cutter assembly 72 is the actuated position. For instance, the second safety mechanism can prevent the tension assembly from moving from the partially engaged position to the tightened position as illustrated, and can alternatively prevent the tension assembly 70 from moving from the disengaged position to the tightened position while cutter assembly 72 is the actuated position. It can thus be said that the second safety mechanism 195 can prevent the tension assembly 70 from moving along a direction from the disengaged position to the tightened position while cutter assembly 72 is the actuated position. In this regard, it should be appreciated that the safety mechanism 110 can be referred to as a first safety mechanism. The second safety mechanism 195 can include at least one safety member 196, such as first and second wings 161a and 161b that extends from the rear end 159 of the spacer member 149, for instance rearward along the longitudinal direction L toward the rear end 78b of the body 76. In other embodiments, the wings 161a and 161b do not extend from a spacer and are otherwise present within fixation instrument 22 and provide the same functionality as wings 161a and 161b that extend from the spacer member 149.

Each wing 161a and 161b can include a respective wing body #a and #b, respectively, and a hook 163a, and 163b, respectively, that extends out, for instance substantially perpendicularly down, from the corresponding wing body #a and # substantially along the transverse direction T. As illustrated in FIG. 12B, each wing 161a and 161b defines a respective laterally outer face 165a and 165b and an opposed laterally inner face 167a and 167b that is spaced from the laterally outer face 165a and 165b along the lateral direction A. Each hook 163a, 163b defines a longitudinally outer, or front, end 169a and 169b, respectively, and an opposed rear end 171a and 171b that is spaced from the front end 169a and 169b along the longitudinal direction L.

Referring to FIG. 12A, the fixation instrument 22 defines a gap 173 that extends between the first and second wings 161a and 161b along the lateral direction A, such as between the inner faces 167a and 167b. The gap 173 is sized so as to receive the cutter arm 106 when the cutter arm 106 is in the disengaged position. For instance, the inner faces 167a and 167b can define respective seats that can support the cutter arm 106 when the cutter arm 106 is in the disengaged position. For instance, the inner faces 167a and 167b can be contoured to abut a complementary outer surface of the cutter arm 106 when the cutter arm 106 is in the disengaged position at the upper transverse face of the body 76. Accordingly, when the cutter arm 106 is seated in the gap 173, the cutter arm 106 can be said to be in a seated disengaged position.

Figure 14:
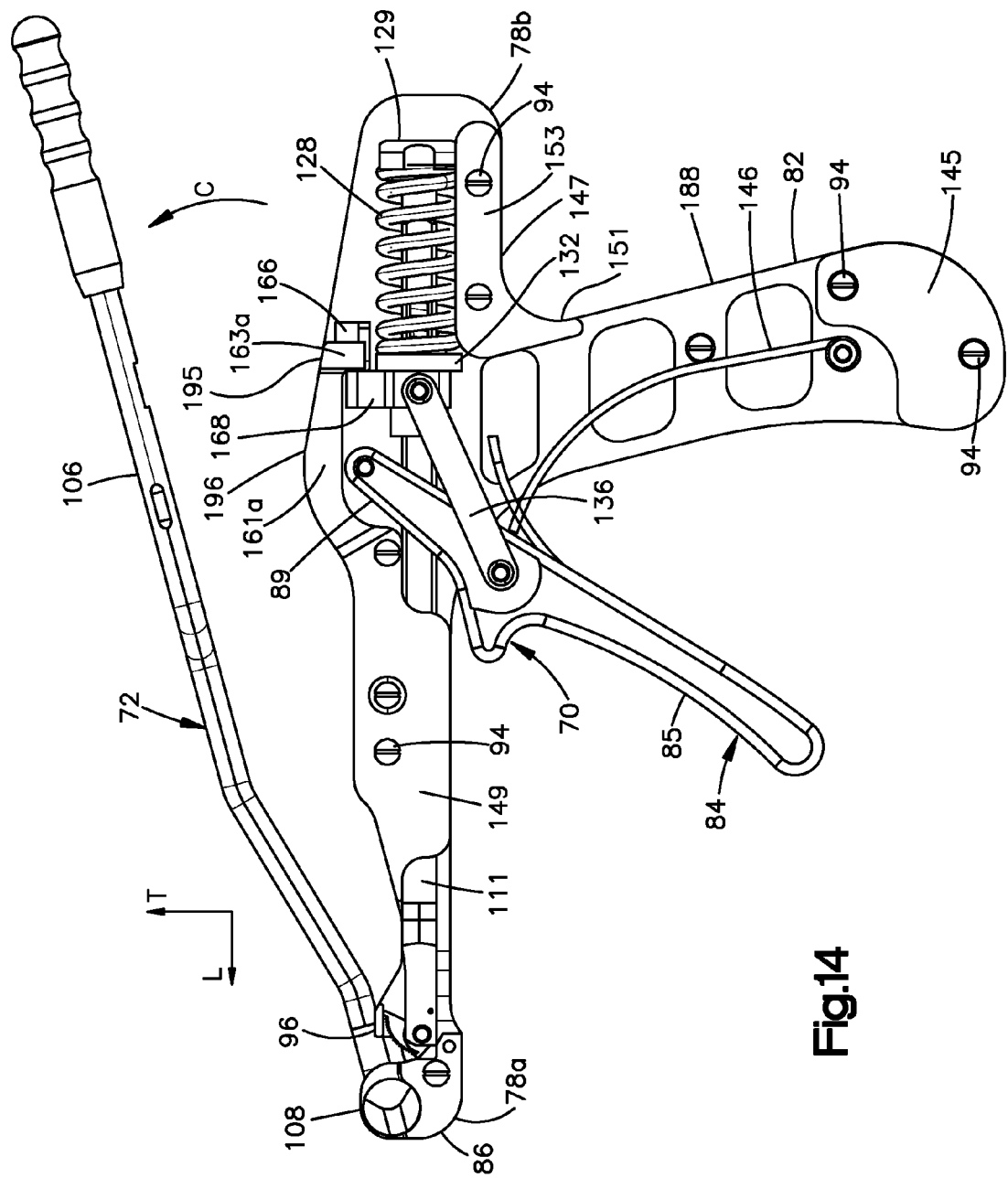
FIG. 14 is a side elevation view of the bone fixation system shown in FIG. 11, showing the tension assembly in a partially engaged position and the cutter arm in an engaged position, and further showing the safety mechanism in an engaged position so as to prevent the tension assembly from moving to the tightened position.
Figure 15A:
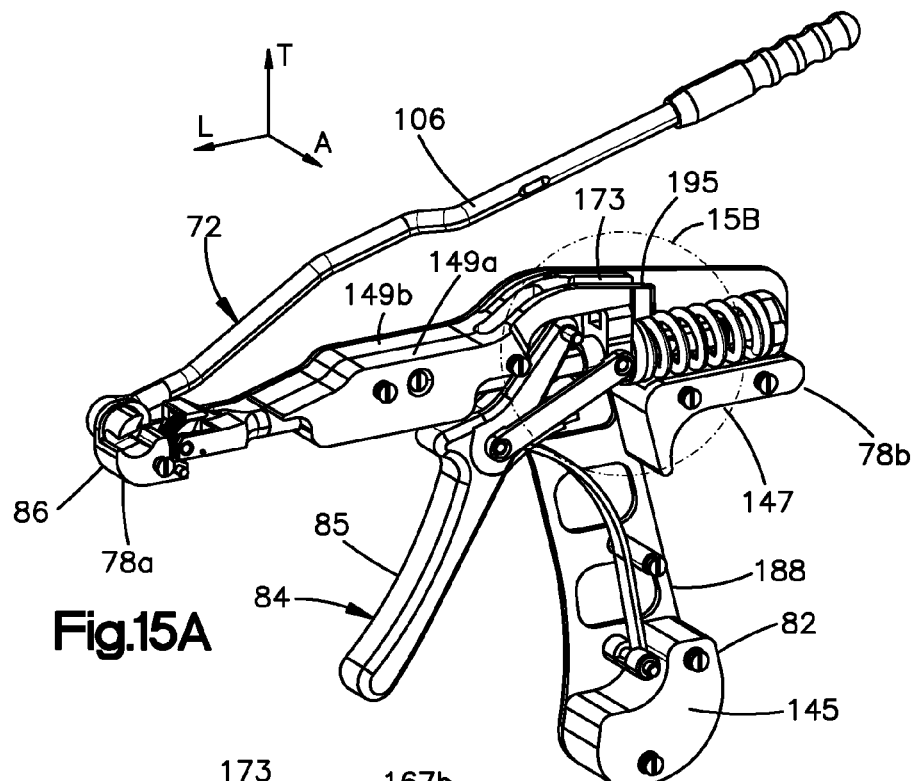
FIG. 15A is a perspective view of the bone fixation system shown in FIG. 14.
Figure 15B:
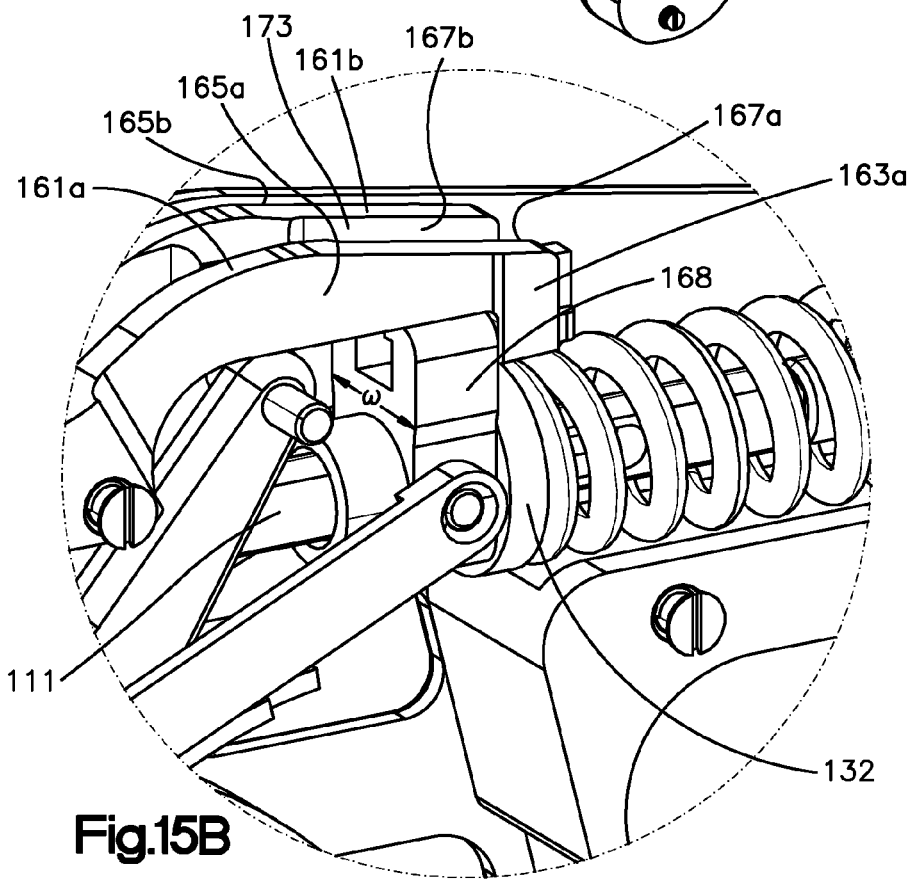
FIG. 15B is a magnified portion of the bone fixation system shown in FIG. 15A, taken along line 15B.

As shown in FIGS. 14 and 15A-B, the cutter arm 106 may be pivotally attached to the body 76, for instance at housing member 190b. In accordance with the illustrated embodiment, the cutter arm 106 is pivotally attached at its front end 107a to the nose 86 at a pivot location 152 that defines a lateral pivot axis. This arrangement is described above and depicted, for example, in FIGS. 7A-B. As shown in FIGS. 5A-B, 14, and 15A-B, cutter arm 106 can be pivoted up and forward about the pivot location 152 along the direction of Arrow C to its engaged position, which causes the cutter blade 108 to travel down along an arc-shaped path toward the complementary cutter blade 87 so as to reduce the size of gap 156. This process is described above. In the embodiments depicted in FIGS. 14 and 15A-B, pivoting of cutter arm 106 from its seated, disengaged position to its engaged position involves removal of cutter arm 106 from the gap 173. Accordingly, when cutter arm 106 is removed the gap 173, the cutter arm 106 can be said to be in an engaged position.

At least one or both of the first and second wings 161a and 161b can be flexible, and can for instance be constructed from a flexible material. Accordingly, at least one or both of the first and second wings 161a and 161b can be movable between an undeflected (or neutral) state and an outwardly deflected (for instance laterally deflected) state. In the undeflected position, shown in FIG. 15B, the first and second wings 161a and 161b are substantially parallel to one another and the gap 173 defines a first distance. The first and second wings 161a and 161b are in the respective undeflected position when the cutter arm 106 is removed from the gap 173, for instance once it is pivoted about the pivot location 152 along the direction of Arrow C to its engaged position. The first and second wings 161a and 161b are in the respective deflected position when the cutter arm 106 is disposed between the first and second wings 161a and 161b in the gap 173. For instance, when the cutter arm 106 is in the seated, disengaged position, it abuts the laterally inner face 167a of the first wing 161a and the laterally inner face 167b of the second wing 161b. As illustrated in FIG. 12B, because the cross-sectional dimension of cutter arm 106 along the lateral direction A is greater than the gap 173 when the first and second wings 161a and 161b are in the undeflected position, when the cutter arm 106 is moved to the seated, disengaged position, the cutter arm 106 biases at least one or both of the first and second wings 161a and 161b away from the other of the first and second wings 161a and 161b to thereby increase the lateral dimension of the gap 173 so that the cuter arm 106 can be seated in the gap 173 as described above. To facilitate the deflection of wings 161a, 161b by cutter arm 106, laterally inner face 167a of wing 161a and laterally inner face 167b of wing 161b may flare laterally inward toward each other as they extend down along the transverse direction T so that the inner faces 167a and 167b can define a non-zero angle with respect to the transverse direction T.

When cutter arm 106 is in the seated, disengaged position, and wings 161a, 161b are deflected laterally outwards, the distance between laterally inner face 167a of wing 161a and laterally inner face 167b of wing 161b along the lateral direction A, and thus the lateral dimension of the gap 173, is greater than the corresponding outer width of the second engagement member 168 along the lateral direction A. FIG. 15B shows the lateral width w of second engagement member, and FIG. 12B shows that the distance between laterally inner face 167a of wing 161a and laterally inner face 167b of wing 161b is greater than the lateral width of second engagement member 168, such that second engagement member 168, along with movable spring seat 132, can travel in a direction along longitudinal direction L towards rear end 78b of body 76 by passing through the gap 173 between laterally inner face 167a of wing 161a and laterally inner face 167b of wing 161b.

By contrast, as shown in FIG. 15B, when cutter arm 106 moves from the seated, disengaged position to the engaged position, one or both of the first and second wings 161a and 161b return to their respective undeflected positions, and the distance between laterally inner face 167a of wing 161a and laterally inner face 167b of wing 161b becomes less than the lateral width of second engagement member 168. As described more fully below, in this configuration, it is not possible for second engagement member 168 to pass between laterally inner face 167a of wing 161a and laterally inner face 167b of wing 161b, and therefore not possible for movable spring seat 132 (from which second engagement member 168 upwardly extends), to travel beyond a certain point towards rear end 78b of body 76 in a direction along longitudinal direction L. It should thus be appreciated that when one or both of the wings 161a and 161b is in the respective undeflected position, the corresponding one or both of the wings 161a and 161b is at least partially aligned with the second engagement member 168 along the longitudinal direction L. Accordingly, the corresponding one or both of the wings 161a and 161b is positioned to abut the second engagement member 168 and prevent the second engagement member 168 from moving through the gap 173. When one or both of the wings 161a and 161b is in the respective deflected position, the wings 161a and 161b are offset with respect to the second engagement member 168 along the lateral direction A, such that the second engagement member 168 is aligned with the gap 173 along the longitudinal direction L, and thus is positioned to move at least into or through the gap 173 past the first and second wings 161a and 161b.

Figure 11:
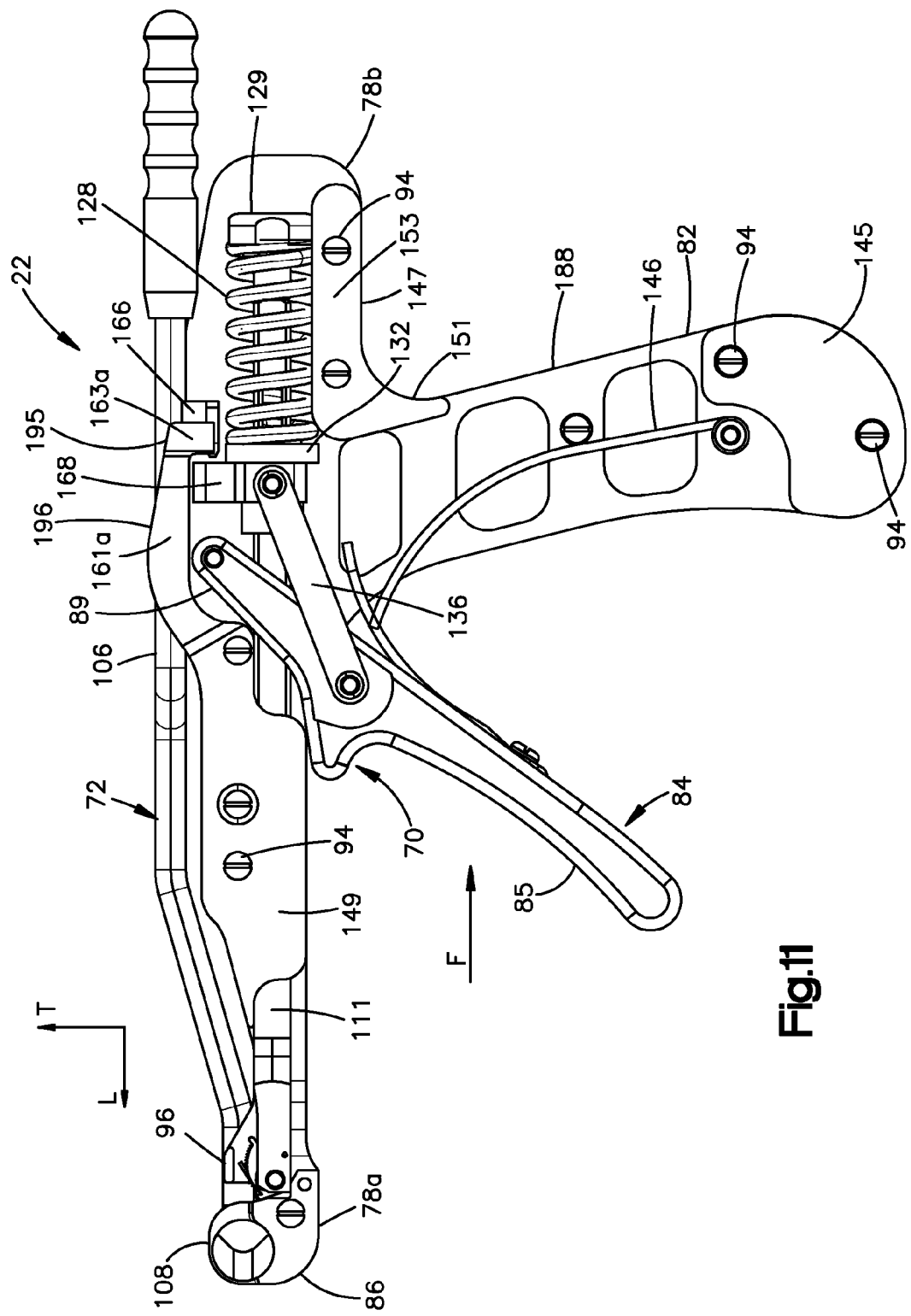
FIG. 11 is a side elevation view of the bone fixation system constructed in accordance with another embodiment, showing both the tension assembly in a disengaged position, and further showing the cutter arm in a disengaged position.
Figure 12:
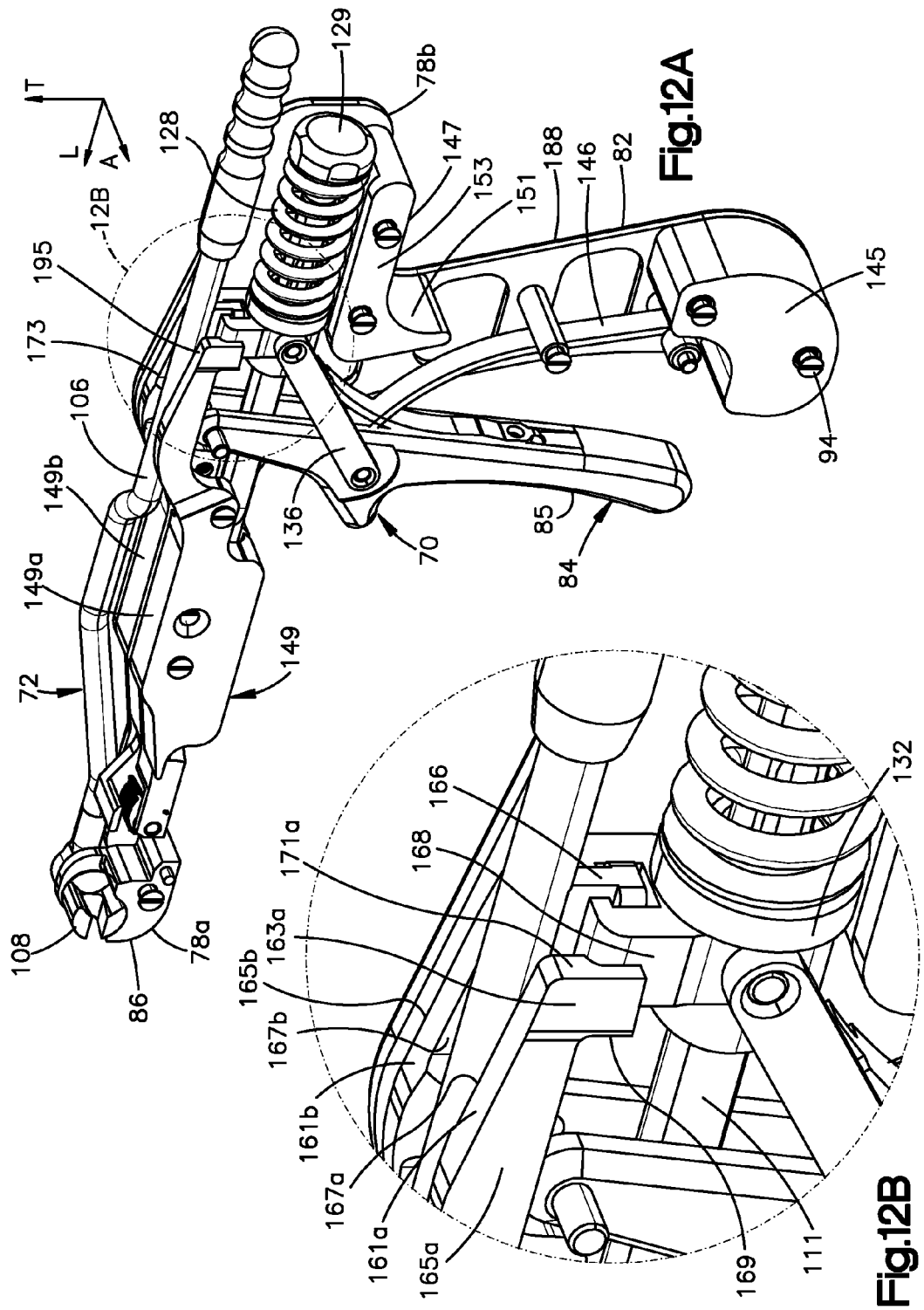
FIG. 12A is a perspective view of the bone fixation system shown in FIG. 11.
FIG. 12B is a magnified portion of FIG. 12A, taken along line 12B.

As illustrated in FIG. 11, when the tension assembly 70 (described previously) is in the first initial position, both of the hooks 163a and 163b and the first engagement member 166 are spaced along the longitudinal direction L, for instance rearward, from the movable spring seat 132 and second engagement member 168, which extends upwardly from movable spring seat 132. When the user applies the actuation force, for instance the rearwardly directed force F, to grip portion 85 of trigger 84, the trigger 85 and thus also the tension assembly 70 move from the first initial position to the second grip position, which causes the movable spring seat 132 to translate rearward along traveler rod 111 in the longitudinal direction towards the rear of end 78b of body 76. As shown in FIGS. 14 and 15A-B, when the cutter arm 106 is in the unseated, engaged position, the first and second wings 161a and 161b are in their respective undeflected positions. Accordingly, when the tension assembly 70 moves from the first initial position to the second grip position, the movable spring seat 132 moves towards the rear end 78 until the second engagement member 168 abuts one or both of the first and second wings 161a and 161b, for instance at the respective front longitudinal ends 169a and 169b of the hooks 163a and 163b. Once second engagement member 168 abuts the hooks 163a and 163b, for instance at the front longitudinal ends 169a and 169b, interference between one or both of the wings 161a and 161b and the second engagement member 168 prevents the tension assembly 70 from moving to the third tension position, for instance from the second grip position, thereby preventing the tension assembly 70 from increasing the tension in the strap 32 while cutter arm 106 is in the unseated, engaged position.

Figure 13:
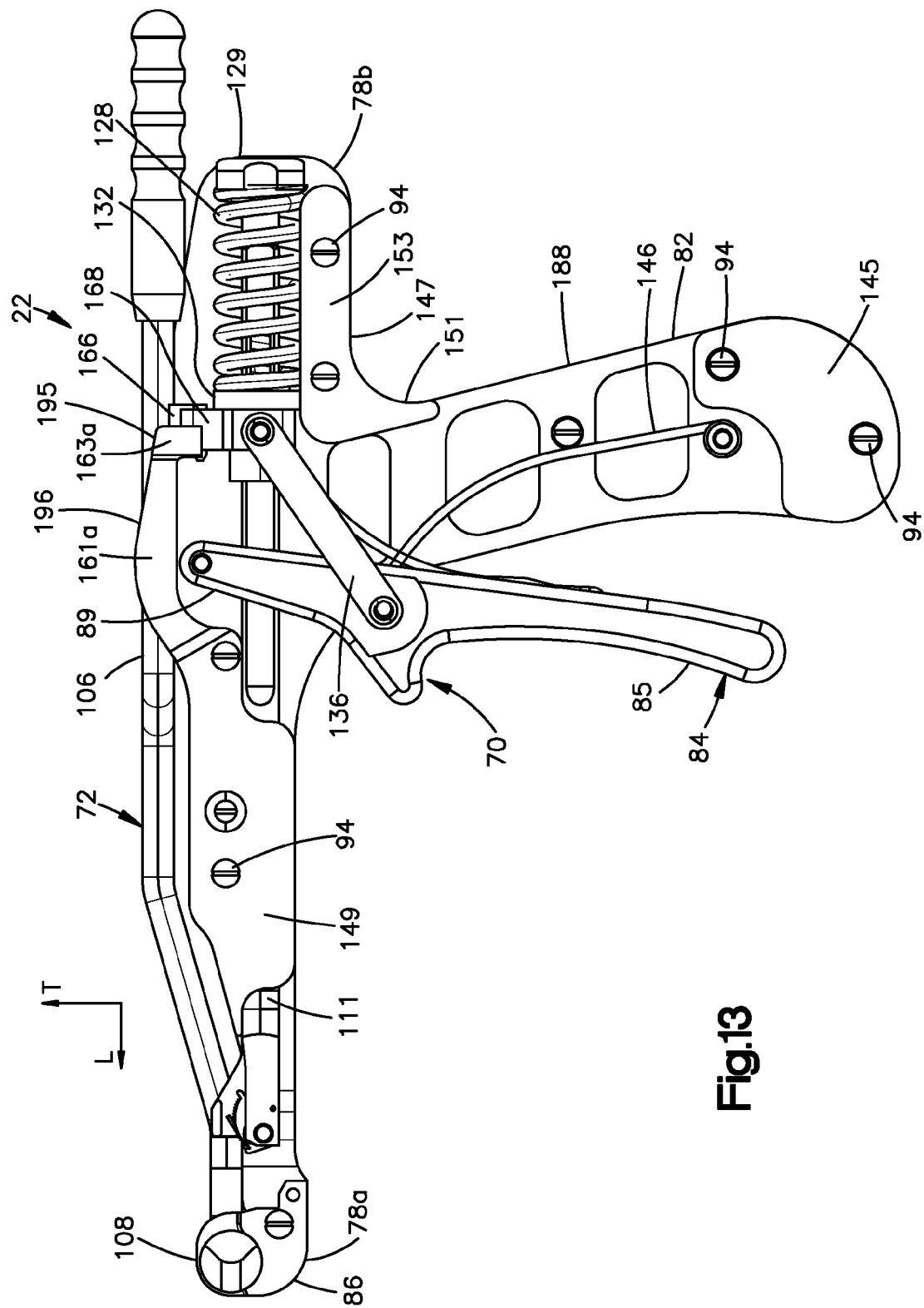
FIG. 13 is a side elevation view of the bone fixation system shown in FIG. 11, showing the tension assembly in a tightened position and the cutter arm in the disengaged position.

On the other hand, as illustrated in FIGS. 12A-B and 13, when the cutter arm 106 is in the seated, disengaged position, the wings 161a and 161b are in their respective deflected positions. Accordingly, when the tension assembly 70 moves from the first initial position to the second grip position, the movable spring seat 132 is movable along the longitudinal direction L, for instance rearwardly toward the rear end 78b, until second engagement member 168 passes at least into or through the gap 173 between the wings 167a and 167b, for instance between the respective laterally inner faces 167a and 167b. Because the wings 161a and 161b are offset from the second engagement member 168 when the wings 161a and 161b are in the deflected position, the second engagement member 168 does not abut the front longitudinal edges 169a and 169b of hooks 163a and 163b, respectively, so as to prevent the second engagement member 168 from traveling into the gap 173. As a result, when the wings 161a and 161b are in the deflected position, the tensioning assembly 70 can be moved from the second grip position to the third tightened position, thereby increasing tension in the strap 32.

As described previously, the first and second engagement members 166 and 168 are positioned so as to interlock when they longitudinally overlap. Thus, in the embodiments depicted in FIGS. 11-15, the first and second engagement members 166 and 168 at least partially overlap when the tension assembly is in the third tension position, thereby defining interference that prevents the cutter arm 106 from becoming unseated and moving to the engagement position along the direction of Arrow C.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone fixation instrument configured to apply tension to a bone fixation member so as to tighten the bone fixation member about a target bone, the fixation instrument comprising:
    a body defining a front end and an opposed rear end;
    a grip configured to secure a free end of the fixation member to the fixation instrument;
    a traveler that is connected to the grip such that the grip moves rearward along with the traveler so as to increase tension in the bone fixation member;
    an actuator operatively coupled to the traveler, the actuator configured to move from an initial position toward a tension position in response to an applied force, thereby biasing the traveler to move rearward;
    a tension limiter operatively connected between the actuator and the traveler, wherein the tension limiter allows the traveler to move rearward when the tension in the bone fixation member is less than a select tension, and prevents the traveler from moving rearward when the tension in the bone fixation member reaches the select tension;
    a cutter assembly configured to move from a disengaged position to an engaged position; and,
    a safety mechanism that is activated by movement of the cutter assembly from the disengaged position to the engaged position in order to prevent the actuator from moving to the tension position.

2. The bone fixation instrument as recited in claim 1, wherein the grip is movable between a disengaged position and an engaged position, such that when the grip is in the disengaged position, the grip defines a gap sized to receive the bone fixation member, and when the grip is in the engaged position, the gap is reduced such that the grip secures the bone fixation member to the bone fixation instrument.

3. The bone fixation instrument as recited in claim 1, wherein the grip further comprises first and second grip members, such that one of the grip members is movable between a disengaged position and an engaged position, such that the movable grip member is spaced apart further from the other grip member in the disengaged position than in the engaged position.

4. The bone fixation instrument as recited in claim 3, wherein the movable grip member moves from the disengaged position to the engaged position when the traveler moves rearward from a forward position.

5. The bone fixation instrument as recited in claim 4, wherein the movable grip member is biased toward the engaged position and engages the body so as to prevent the movable grip member from moving from the disengaged position to the engaged position when the traveler is in the forward position.

6. The bone fixation instrument as recited in claim 5, wherein when the traveler moves rearward from the forward position, the movable grip member becomes disengaged from the body and is biased to the engaged position.

7. The bone fixation instrument as recited in claim 1, wherein the tension limiter comprises a spring member operatively connected between the actuator and the traveler, wherein movement of the actuator causes the spring member to flex and bias the traveler rearward under a biasing force.

8. The bone fixation instrument as recited in claim 7, wherein the traveler moves rearward when the biasing force is greater than the tension in the bone fixation member.

9. The bone fixation instrument as recited in claim 8, wherein the traveler remains stationary when the biasing force is not greater than the tension in the bone fixation member.

10. The bone fixation instrument as recited in claim 7, further comprising a force transfer member coupled between the actuator and the spring member, wherein movement of the actuator moves the force transfer member to flex the spring member.

11. The bone fixation instrument as recited in claim 10, wherein the spring member is coupled to a movable spring seat that is connected to the force transfer member.

12. The bone fixation instrument as recited in claim 7, wherein the spring compresses as the actuator moves from the initial position toward the tension position, and the compression of the spring causes the spring to bias the traveler to move rearward.

13. The bone fixation instrument as recited in claim 7, wherein the actuator is movable from the initial position to a second position that causes the spring to flex to a position that biases the traveler rearward and causes the grip to secure to the bone fixation member prior to increasing the tension in the bone fixation member.

14. The bone fixation instrument as recited in claim 1, wherein the actuator is movable from the initial position to a second position that causes the grip to secure to the bone fixation member, and from the second position to the tension position that causes the traveler to move and increase the tension in the bone fixation member.

15. The bone fixation instrument as recited in claim 14, wherein the actuator moves from the initial position to the second position to the tension position in one continuous motion.

16. The bone fixation instrument as recited in claim 1 whereby the cutter assembly cuts the free end of the bone fixation member when in the engaged position.

17. The bone fixation instrument as recited in claim 1, further comprising a second safety mechanism that prevents the cutter assembly from moving from the disengaged position to the engaged position when the traveler has moved rearward so as to increase tension in the bone fixation member.

18. The bone fixation instrument according to claim 1 wherein said cutter assembly is configured to cut the free end of the bone fixation member independently of whether the tension in the bone fixation member has reached the select tension.

19. A bone fixation system comprising:
   at least one bone fixation member including a strap and a locking mechanism, wherein
   the strap can be pulled through the locking mechanism along a first direction so as to form a loop about a target bone, and the locking mechanism prevents the strap from moving therethrough along a second direction opposite the first direction, wherein the strap defines a free end that extends out the locking mechanism; and
   a bone fixation instrument configured to apply tension to the loop about the target bone, the fixation instrument including:
      a tension assembly configured to secure the free end to the fixation instrument, and further configured to pull the free end so as to increase tension in the loop while the tension in the loop is less than a select tension, wherein the tension assembly is unable to further increase tension in the bone fixation member once the tension in the bone fixation member has reached the select tension;
      a cutter assembly that is configured to move from a disengaged position to an engaged position and to cut the free end of the bone fixation member so as to separate the free end from the loop; and,
      a safety mechanism that is activated by movement of the cutter assembly from the disengaged position to the engaged position in order to prevent the tension assembly from further increasing tension in the bone fixation member.

20. The bone fixation instrument according to claim 19 wherein said cutter assembly is configured to cut the free end of the bone fixation member independently of whether the tension in the bone fixation member has reached the select tension.

\* \* \* \* \*